US006245541B1

(12) United States Patent
Houtz

(10) Patent No.: US 6,245,541 B1
(45) Date of Patent: Jun. 12, 2001

(54) ISOLATED SPINACH RIBULOSE-1,5-BISPHOSPHATE CARBOXYLASE/OXGENASE LARGE SUBUNIT ε N-METHYLTRANSFERASE AND METHOD OF INACTIVATING RIBULOSE-1,5-BISHOSPHATASE ε N-METHYLTRANSFERASE ACTIVITY

(75) Inventor: Robert L. Houtz, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/138,614

(22) Filed: Aug. 24, 1998

Related U.S. Application Data

(63) Continuation of application No. 08/687,916, filed on Jul. 29, 1996, now Pat. No. 5,908,972, which is a continuation-in-part of application No. 08/391,000, filed on Feb. 21, 1995, now Pat. No. 5,723,752.

(51) Int. Cl.$^7$ ............... C12N 9/10; C12N 1/20; C07H 21/04
(52) U.S. Cl. ............ 435/193; 435/252.3; 435/320.1; 435/468; 435/69.1; 435/70.1; 536/23.2; 536/23.6; 800/278; 800/285; 800/298; 530/350
(58) Field of Search ............... 435/193, 252.3, 435/320.1, 468, 69.1, 70.1; 536/23.2, 23.6; 800/278, 285, 298; 530/350

(56) References Cited

PUBLICATIONS

Anderson et al. J. Biol. Chem. 258(23): 14088–14090, 1983.*
Black et al., "Light–regulated Methylation of Chloroplast Proteins," The Journal of Biological Chemistry 262(20):9803–07 (1987).
Houtz et al., "Affinity Purification of Ribulose 1,5–Bisphosphate Carboxylase/Oxygenase Large Subunit εN–Methyl–Transferase," Supplement to Plant Physiology, Annual Meeting of Plant Physiologists (1992).
Houtz et al., "Identification and Specificity of Ribulose 1,5–Bisphosphate Carboxylase/Oxygenase Large Subunit ε-N-methyltransferase," Supplement to Plant Physiology, Annual Meeting of Plant Physiologists (1992).
Napoli et al., "Introduction of a Chimeric Chalcone Synthase Gene into Petunia Results in Reversible Co–Suppression of Homologous Genes in trans," The Plant Cell, 2:279–89 (1990).
Smith et al., "Antisense RNA inhibition of polygalacturonase gene expression in transgernic tomatoes," Nature, 334:724–26 (1988).
Niemi et al., "Protein Methylation in Pea Chloroplasts," Plant Physiol., 93:1235–40 (1990).
Houtz et al., "Partial Purification and Characterization of Ribulose–1,5–bisphosphate Carboxylase/Oxygenase Large Subunit εN–Methyltransferase," Plant Physiol., 97:913–20 (1991).

Eckes et al., "Isolation and characterizationof a light–inducible, organ–specific gene from potato and analysis of its expression after tagging and transfer into tobacco and potato shoots," Mol. Gen. Genet., 205:14–22 (1986).
Klein et al., "Cloning and development expression of the sucrose–phosphate–synthase gene from spinach," Planta, 190:498–510 (1993).
Houtz et al., "Partial Amino Acid Sequence of Ribulose–1, 5–Bisphosphate Carboxylase/Oxygenase Large Subunit εN–Methyl–Transferase," Supplement to Plant Physiology, 102(1):47 (1993).
Klein et al., "Cloning and Expression of the Rubisco Large Subunit Methyl–Transferase Gene from Pea," Supplement to Plant Physiology, 105(1):85 (1994).
Klein et al., "Cloning and development expression of pea ribulose–1,5–bisphosphate carboxylase/oxygenase large subunit N–methyltransferase," Plant Molecular Biology, 27:249–61 (1995).
Wang et al., "Affinity Purification of Ribulose–1,5–bisphosphate Carboxylase/Oxygenase Large Subunit εN–Methyltransferase," Protein Expression and Purification, 6:528–36 (1995).
Ying et al., "Molecular Rationale for the Absence of Methylation at Lysyl at Lysyl Residue 14 in the Large Subunit of Spinach Rubisco," Plant Phsiology (Supplement), 111(2): (Jun. 1, 1996).
Houtz et al., "Posttranslation Modifications in the Amino–Terminal Region of the Large Subunit of Ribulose–1,5–Bisphosphate Carboxylase/Oxygenase from Several Plant Species," Plant Physiology, 98:1170–74 (1992).
Houtz et al., "Post–Translational modifications in the large subunit of ribulose bisphosphate carboxylase/oxygenase," Proc. Natl. Acad. Sci. USA, 86:1855–59 (Mar. 1989).
Mulligan et al., "Reaction–intermediate analogue binding by ribulose bisphosphate carboxylase/oxygenase causes specific changes in proteolytic sensitivity: The amino–terminal residue of the large subunit is acetylated proline," Proc. Natl. Acad. Sci., USA, 85:1513–17 (Mar. 1988).
Ying et al., "Organization and characterization of the ribulose–1,5–bisphosphate carboxylase/oxygenase large subunit εN–methyltransferase gene in tobacco," Plant Molecular Biology, 32:663–71 (1996).

* cited by examiner

*Primary Examiner*—Tekchand Saidha
(74) *Attorney, Agent, or Firm*—Burns, Doane, Swecker & Mathis, L.L.P.

(57) ABSTRACT

The gene sequence for ribulose-1,5-bisphosphate carboxylase/oxygenase (Rubisco) large subunit (LS) $^{\epsilon}$N-methyltansferase (protein methylase III or Rubisco LSMT) from a plant which has a des(methyl) lysyl residue in the LS is disclosed. In addition, the full-length cDNA clones for Rubisco LSMT are disclosed. Transgenic plants and methods of producing same which have the Rubisco LSMT gene inserted into the DNA are also provided. Further, methods of inactivating the enzymatic activity of Rubisco LSMT are also disclosed.

4 Claims, 15 Drawing Sheets

```
                                                                              SF-1
                              AATTCCTAATCTCAAAGTGAGCTAAAA          31
ATGGCAACTTTATTCACTCTCATCCCTCATCAAACTTCTCAACCTTTCAAA                91
 M  A  T  L  F  T  L  I  P  S  S  N  S  T  F  L  N  P  F  K       20
 M  A  T  L  F  T  L  L  P  S  S  N  S  T  F  L  N  P  F  K       20

ACCACCCAACACTCCAAACTTCATTTCGCAACCCATCTCCCACCTTCAAAAACCCGCTC       151
 T  T  Q  H  S  K  L  H  F  A  T  P  S  P  T  F  K  N  P  L       40
 T  T  Q  H  S  K  L  H  F  A  T  P  S  P  T  F  K  N  P  L       40
        SR-10

TCAATCAGATGTTTCCGGCCACCGGAAACCGATACACCACCGGAAATCCAGAAATTCTGG      211
 S  I  R  C  F  R  P  P  E  T  D  T  P  P  E  I  Q  K  F  W       60
 S  I  R  C  F  R  P  P  E  T  D  T  P  P  E  I  Q  K  F  W       60

GGTTGGCTTTCCGACAAAGGAATTATCTCACCAAAATGCCCTGTAAAACCAGGTATTGTC     271
 G  W  L  S  D  K  G  I  I  S  P  K  C  P  V  K  P  G  I  V       80
 G  W  L  S  D  K  G  I  I  S  P  K  C  P  V  K  P  G  I  V       80
                                        SF-2

CCAGAAGGATTAGGACTAGTAGCCCAAAAGATATCCAGAAACGAGGTCGTTTGGAG         331
 P  E  G  L  G  L  V  A  Q  K  D  I  S  R  N  E  V  V  L  E      100
 P  E  G  L  G  L  V  A  Q  K  D  I  S  R  N  E  V  V  L  E      100

GTGCCCCAGAAGTTTTGGATAAACCCAGATACAGTTGCAGCTTCAGAGATTGGGTCAGTT     391
 V  P  Q  K  F  W  I  N  P  D  T  V  A  A  S  E  I  G  S  V      120
 V  P  Q  K  F  W  I  N  P  D  T  V  A  A  S  E  I  G  S  V      120

TGTAATGGGCTTAAGCCTTGGGTTTCTGTGGCTTTGTTTCTGATGAGAGAAAAATTG         451
 C  N  G  L  K  P  W  V  S  V  A  L  F  L  M  R  E  K  K  L      140
 C  N  G  L  K  P  W  V  S  V  A  L  F  L  M  R  E  K  K  L      140
```

FIG. 2A

```
GGGAATTCTTCATCTTGGAAACCTTACATTGATATTTGCCTGATTCTACTAATTCAACA      511
 G  N  S  S  S  W  K  P  Y  I  D  I  L  P  D  S  T  N  S  T     160
 G  N  S  S  S  W  K  P  Y  I  D  L  P  D  D  S  T  N  S  T     160
                                                   SF-3
ATTTATTGgtatgttttttggtaaattgactggtttagtttctggtagcttttatg          571
 I  Y  W                                                         163
 I  Y  W                                                         163
        ──────────────────▶
              SR-9
tttgcaatcttaattggtggattaagctaaatgaagtttggttgttgcttt               631
              ◀──────────────────
                    SF-4
gcagagcagGTCAGAGAGGAACTCTGAGCTTCAAGgttagtttcgattttcgactta         691
          S  E  E  E  L  S  E  L  Q  G                           173
          S  E  E  E  L  S  E  L  Q  G                           173
                                   ──────────────────▶
                                          SF-5
gagttgcttgtgattatgctattcaaaagtgcttgtgattattggtatgtttttgggtt       751
agtttgatgtttagttttagctttattgtttgcaattttatgtgtaaatggttaatggtgatt   811
tagtgtcgcattactaactcgattgcgctatcgattcagttcgctatcatgtaaatgttcc     871
gagtgttttactaacttcgtccagattcagttctgacattaattaatcactgtca           931
ttgtgagcatgtttctgtacagagggagtatcatctgttttatttgagttgaagatt         991
                                        ◀──────────────────
                                                SR-8
agttttggtgtatggaaatcgaatcgaatgctggtgtactggtgtcgtagtgttac          1051
actgcttataaatccaataggaggaggtggtatcaaatatctgcagccttacgttga         1111
cattgttctctattcttttcttttgtcaatgttttaacgcttcgtatttgatgaaggaagga   1171
```

FIG. 2B

```
aatcgtgcatatctcccagtatttgaaactttttgcaccttgacctaaacagttgtcta    1231
tgtagagacttatatttcaattccattcaaaacaccggtactctagtattcatgtcgat   1291
ttgatgtactagttttatgattcttttgaacttctacgcgtctggtaaagggtcatcgat  1351
                                              SF-6 →
ctctgctttttcaaacagcttcacatcaaacttggcacttcattgtcattattgttattc  1411
                           ← SR-7 ctacacgggggttgacttgggagcaaggagctctccagagttgtacgtagtatcatcaatg 1471
tcgtattatatgtctgtgttgaagtctgttttaattgtacggtagtatctttgttgaatga 1531
agaatgttagtagtatagatctgtttttaattgtgtttagaggtatgttaaatttgga    1591
aattggttcaacgctaaaacactctattgaccctgttcagagaaataatcaatatgt     1651
agacaatgaaggttttctttgctgtagtttcaaatttgcctacttcacagtgatctat    1711
                                                SF-7 →
aagactataatcttgcagGTAGTCAGTTGCTGAACACAACATTGGGTGTGAAGGAGTTA    1771
                    S   Q   L   L   N   T   T   L   G   V   K   E   L        186
                    S   Q   L   L   N   T   T   L   G   V   K   E   L        186
                              ← SR-6
GTAGCAAATGAGTTTGCAAAACTGGAAGAAGTACTAGTTCCCCACAAGCAACTATTC      1831
  V   A   N   E   F   A   K   L   E   E   E   V   L   V   P   H   K   Q   L   F     206
  V   A   N   E   F   A   K   L   E   E   E   V   L   V   P   H   K   Q   L   F     206
                                                                 SF-8* →
CCTTTGATGTAACTCAAGATGACTTCTTTTGGGCATTGGAATGCTGCGATCAAGAGCA     1891
  P   F   D   V   T   Q   D   D   F   F   W   A   F   G   M   L   R   S   R   A     226
  P   F   D   V   T   Q   D   D   F   F   W   A   F   G   M   L   R   S   R   A     226

TTCACTTGTCTTGAGGGCCAAGTCTCTTGTTCTAATCCCCTTGCCGATTTGgtaatcatc  1951
  F   T   C   L   E   G   Q   S   L   V   L   I   P   L   A   D   L              243
  F   T   C   L   E   G   Q   S   L   V   L   I   P   L   A   D   L              243
```

FIG. 2C

```
tttcctgttcctaatttcattataaaaaaaaaaacatgtactttctcatgttat          2011
gcattatacatgatgaatatttattttaacatgtaaagTGGGTGCAACAGGCTAACCACAG   2071
                                      W  V  Q  Q  A  N  H  S   251
                                                A  N  H  S      247
                                              SR-5
                                              ←――――――――――
TCCTGATATAACAGCACCGAAGTATGCTTGGGAAATCAGAGGAGCTGGTCTATTCTCTAG    2131
 P  D  I  T  A  P  K  Y  A  W  E  I  R  G  A  G  L  F  S  R    271
 P  D  I  T  A  P  K  Y  A  W  E  I  R  G  A  G  L  F  S  R    267

AGAACTTGTATTTTCACTGAGGAATCCAACCCCAGTTAAGGCTGGTGACCAGgtagtgtt   2191
 E  L  V  F  S  L  R  N  P  T  P  V  K  A  G  D  Q            288
 E  L  V  F  S  L  R  N  P  T  P  V  K  A  G  D  Q            284 ttttctctcgaatcgaacaatgaagtatataagtcacttaagtttaatgtcaactgct      2251

GTTCTGATCCAATACGATT      2311
                                        V  L  I  Q  Y  D  L     295
                                        V  L  I  Q  Y  D  L     291
                                       ――――――――――→
                                            SR-4

TGAACAAGAGCAATGCGGAATTAGCCTTGGATTATGGGGTTGACGGAATCCAGATCAGAAA  2371
 N  K  S  N  A  E  L  A  L  D  Y  G  L  T  E  S  R  S  E  R    315
 N  K  S  N  A  E  L  A  L  D  Y  G  L  T  E  S  R  S  E  R    311
―――――――→
  SF-9

GAAATGCATACACCCTAACACTGGAAATACCCGAATCAGATTCTTTTACGGGGACAAGC    2431
 N  A  Y  T  L  T  L  E  I  P  E  S  D  S  F  Y  G  D  K  L    335
 N  A  Y  T  L  T  L  E  I  P  E  S  D  S  F  Y  G  D  K  L    331
```

FIG. 2D

```
TAGACATAGCTGAGTCAAATGGGGGAAAGTGCCTACTTTGATATTGTTTAGAAC     2491
 D   I   A   E   S   N   G   M   G   E   S   A   Y   F   D   I   V   L   E   Q       355
 D   I   A   E   S   N   G   M   G   E   S   A   Y   F   D   I   V   L   E   Q       351

AGCCACTTCCTGCAAATATGCTACGATATTGAGGCTTGTTGCACTTGGTGGAGAAGATG     2551
 P   L   P   A   N   M   L   P   Y   L   R   L   V   A   L   G   G   E   D   A       375
 P   L   P   A   N   M   L   P   Y   L   R   L   V   A   L   G   G   E   D   A       371

CTTTTCTGTTGGAGTCTATATTCAGGAACTCTATATGGGGACATCTTGATCTTCCTATTA     2611
 F   L   L   E   S   I   F   R   N   S   I   W   G   H   L   D   L   P   I   S       395
 F   L   L   E   S   I   F   R   N   S   I   W   G   H   L   D   L   P   I   S       391
                                                                    SR-3
GCCCTGCCAATGCGGAGCTCATATGCCAAGTGATTCGTGATGCTTGTACATCTGCTCTT     2671
 P   A   N   E   E   L   I   C   Q   V   I   R   D   A   C   T   S   A   L   S       415
 P   A   N   E   E   L   I   C   Q   V   I   R   D   A   C   T   S   A   L   S       411
             SF-10                                              ←
CTGGTTACAGTACTACAATTGCAGAGgtaactcaatatggttttatagtattgatttat     2731
 L   V   T   V   L   Q   L   Q   R                                                    423
 L   V   T   V   L   Q   L   Q   R                                                    419
          →
ctctctttgttataacaagaatgtgttgttattttttattaatgtagGATGAGAAGCTGT     2791
                                                D   E   K   L   L                     428
                                                D   E   K   L   L                     424

TAGCAGAAGGTGATATAGATCCGAGGCTTGAGATTGCTATAACTATAAGGTTAGGGGAAA     2851
 A   E   G   D   I   D   P   R   L   E   I   A   I   T   I   R   L   G   E   K       448
 A   E   G   D   I   D   P   R   L   E   I   A   I   T   I   R   L   G   E   K       444
```

FIG. 2E

```
SPINACH40  MATLFTLIPS-SNSTFLNPFKTTQHSKLHFATPSPTFKNPLSIRCFRPPETDTPPEIQKFWGW   62
SPINACH38  MATLFTLIPS-SNSTFLNPFKTTQHSKLHFATPSPTFKNPLSIRCFRPPETDTPPEIQKFWGW   62
PEA        MATIFSGG---SVSPFLFHTNKGTSFTPKAPILHLKRSFSAKSVASVGTEPSLSPAVQTFWKW   60
TOBACCO    MASVFSVHPLPSSSFLCPLKTTKSRTKHHQTFYTYQKTILINSLQLTELDPKIPQPVQTFWQW   63

SPINACH40  LSDKGIISPKCPVKPGIVPEGLGLVAQKDISRNEVVLEVPQKFWINPDTVAASEIGSVCNGLK  125
SPINACH38  LSDKGIISPKCPVKPGIVPEGLGLVAQKDISRNEVVLEVPQKFWINPDTVAASEIGSVCNGLK  125
PEA        LQEEGVITAKTPVKASVVTEGLGLVALKDISRNDVILQVPKRLWINPDAVAASEIGRVCSELK  123
TOBACCO    LCKEGVVTKTPVKPGIVPEGLGLVAKRDIAKGETVLQVPKRFWINPDAVAESEIGNVCSGLK  126

SPINACH40  PWVSVALFLMREKKLGNSSSWKPYIDILPDSTNSTIYWSEEELSELQGSQLLNTTLGVKELVA  188
SPINACH38  PWVSVALFLMREKKLGNSSSWKPYIDILPDSTNSTIYWSEEELSELQGSQLLNTTLGVKELVA  188
PEA        PWLSVILFLIRER-SREDSVWKHYFGILPQETDSTIYWSEEELQELQGSQLLKTTVSVKEYVK  185
TOBACCO    PWISVALFLLREK-WRDDSKWKYYMDVLPKSTDSTIYWSEEELSEIQGTQLLSTTMSVKDYVQ  188
```

FIG. 3A

```
SPINACH40  NEFAKLEEEVLVPHKQLFPFDVTQDDFFWAFGMLRSRAFTCLEGQSLVLIPLADLWVQQANHS  251
SPINACH38  NEFAKLEEEVLVPHKQLFPFDVTQDDFFWAFGMLRSRAFTCLEGQSLVLIPLADL----ANHS  247
PEA        NECLKLEQEIILPNKRLFPDPVTLDDFFWAFGILRSRAFSRLRNENLVVVPMADL----INHS  244
TOBACCO    NEFQKVEEEVILRNKQLFPFPITLDDFFWAFGILRSRAFSRLRNQNLILVPFADL----TNHN  247

SPINACH40  PDITAPKYAWEIRG-AGLFSRELVFSLRNPTPVKAGDQVLIQYDLNKSNAELALDYGLTESRS  313
SPINACH38  PDITAPKYAWEIRG-AGLFSRELVFSLRNPTPVKAGDQVLIQYDLNKSNAELALDYGLTESRS  209
PEA        AGVTTEDHAYEVKGAAGLFSWDYLFSLKSPLSVKAGEQVYIQYDLNKSNAELALDYGFIEPNE  307
TOBACCO    ARVTTEDHAHEVRGPAGLFSWDLLFSLRSPLKLKAGDQLFIQYDLNKSNADMALDYGFIEPSS  310

SPINACH40  ERNAYTLTLEIPESDSFYGDKLDIAESNGMGESAYFDIVLEQPLPANMLPYLRLVALGGEDVF  376
SPINACH38  ERNAYTLTLEIPESDSFYGDKLDIAESNGMGESAYFDIVLEQPLPANMLPYLRLVALGGEDVF  372
PEA        NRHAYTLTLEISESDPFFDDKLDVAESNGFAQTAYFDIFYNRTLPPGLLPYLRLVALGTDAF   370
TOBACCO    ARDAFTLTLEISESDEFYGDKLDIAETNGIGETAYFDIKIGQSLPPTMIPYLRLVALGGTDAF  373
```

FIG. 3B

| | | |
|---|---|---|
| SPINACH40 | LLESIFRNSIWGHLDLPISPANEELICQVIRDACTSALSGYSTTIAEDEKLLAEGDIDPRLEI | 439 |
| SPINACH38 | LLESIFRNSIWGHLDLPISPANEELICQVIRDACTSALSGYSTTIAEDEKLLAEGDIDPRLEI | 435 |
| PEA | LLESIFRNSVWGHLGLPVSRANEELICKVVRDACKSALSGYHTTIEEDEKLMEEGNLSTRLQI | 436 |
| TOBACCO | LLESLFRDTIWGHLELSVSRDNEELLCKAVREACKSALAGYHTTIEQDREL-KEGNLDSRLAI | 432 |
| | | |
| SPINACH40 | AITIRLGEKKVLQQIDEEFKEREMELGGYEYYQERRLKDLGLAGEQGEKLPWIGEV | 495 |
| SPINACH38 | AITIRLGEKKVLQQIDEEFKEREMELGGYEYYQERRLKDLGLAGEQGEKLPWIGEV | 491 |
| PEA | AVGIREGEKMVLQQIDGIFEQKELELDQLEYYQERRLKDLGLCGENGDILGDLGKFF | 489 |
| TOBACCO | AVGIRLGEKRVLKQIDDIFRERELELDELEYYGERRLKDLGLVGEQGDIIFWEPK | 491 |

FIG. 3C

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

Trp Val Gln Gln
1

(2) INFORMATION FOR SEQ ID NO: 2:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

TGGGTGCAAC AG            12

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Trp Ala Phe Gly Ile Leu Arg Ser Arg Ala
1           5                 10

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CGATGGCGAT TTGGAATTCT CAGATCAAGG GC        32

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Glu Arg Arg Leu Lys Asp Leu Gly Leu Ala
1           5                 10

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GGCCAAGGCC AAGATCTTTA AGCCTCCTTT C         31

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCTAAGCTTC TAGAGCTCGG GGGGGGGG                                                  28

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GGCCACGCGT CGACTAGTAC T                                                         21

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

AGTCCCGGGT GCAACAGATT AACCACAGTG CAGGAGTTAC                                     40

(2) INFORMATION FOR SEQ ID NO: 10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

AGTTTTAAAG GTCTGCCATT GGAACCAC                                                  28

(2) INFORMATION FOR SEQ ID NO: 11:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CTTTTTCTC                                                                        9

(2) INFORMATION FOR SEQ ID NO: 12:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 12:

TCTTTTTCCT TGTTCCT                                                         17

(2) INFORMATION FOR SEQ ID NO: 13:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

TCTTTTTGTT                                                                 10

(2) INFORMATION FOR SEQ ID NO: 14:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 14:

TTTTTTTTCT C                                                               11

(2) INFORMATION FOR SEQ ID NO: 15:

(i) SEQUENCE CHARACTERISTICS:
            (A) LENGTH: 3144 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

AATTCCTAAT CTCAAAGTGA GTGAGCTAAA AATGGCAACT TTATTCACTC TCATCCCCTC          60

ATCAAACTCT ACCTTTCTCA ACCCTTTCAA AACCACCCAA CACTCCAAAC TTCATTTCGC         120

AACCCCATCT CCCACCTTCA AAAACCCGCT CTCAATCAGA TGTTTCCGGC CACCGGAAAC         180

CGATACACCA CCGGAAATCC AGAAATTCTG GGGTTGGCTT TCCGACAAAG GAATTATCTC         240

ACCAAAATGC CCTGTAAAAC CAGGTATTGT CCCAGAAGGA TTAGGACTAG TAGCCCAAAA         300

AGATATATCC AGAAACGAGG TCGTTTTGGA GGTGCCCCAG AAGTTTTGGA TAAACCCAGA         360

TACAGTTGCA GCTTCAGAGA TTGGGTCAGT TTGTAATGGG CTTAAGCCTT GGGTTTCTGT         420

GGCTTTGTTT CTGATGAGAG AGAAAAAATT GGGGAATTCT TCATCTTGGA AACCTTACAT         480

TGATATTTTG CCTGATTCTA CTAATTCAAC AATTTATTGG TATGTTTTTT TGGTAAATTT         540

GACTGGTTTT AGTTTCTGGG TAGCTTTTAT GTTTGCAATC TTAATTGTTT AATTGGTGGA         600

TTTAAGCTAA ATGAAGTTTG GTTGTTGCTT TGCAGAGCAG GTCAGAAGAG GAACTCTCTG         660

AGCTTCAAGG TTAGTTTCGA TTTTCGACTT AGAGTTGCTT GTGATTATGC TATTCAAAAG         720

TGCTTGTGAT TATTGGTATG TTTTTTGGGT TAGTTTGATG TTTTTAGTTT AGCTTTTATG         780

TTTGCAATTT TAACGGTTTA ATTGGTGGAT TTAGTTGTCG CATTACTAAC TCGATTGCGC         840

```
TATCATGCTG TAAATGTTAT CCGGAAGATG GGAGTGTTTT TACTAACTTC GTCCAGATTC    900
AGTTCTGACA TTAATAATTT AATCACTGTC ATTGTGAGCA TGTTTTCTGT ACAGAGGGAG    960
TATCATCTGT TTTTATTTTG AGTTGAAGAT TAGTTTTTGG TGTATGGAAA TCTGAATCGA   1020
ATGCTGGTGT ACTATGTTGT CGTAGTGTTA CACTGCTTAT AAATCCAATA GGGAGGAGGT   1080
GGTGTATCAA ATATCTGCAG CCTTACGTTG ACATTGTTTC TCTATTTCTT TTGTCAATGT   1140
TTTAACGCTT CGTATTTGAT GAAGGAAAGG AAATCGTGCA TATCTCCCAG TATTTGAAAC   1200
TTTTTGCACC TTGACCTAAA CAGTTGGTCT ATGTAGAGAC TTATATTCAA TTTTCCATTC   1260
AAAACACCGG TACTCTAGTA TTCATGTCGA TTTGATGTAC TAGTTTTATG ATTCTTTGAA   1320
CTTTCTACGC GTCTGGTAAA GGGTCATCGA TCTCTGCTTT TCAAACAGCT TCACATCAAA   1380
CTTGGCACTT CATTGTCATT ATTTGTTATT CCTACACGGG GTTGGACTTG GGAGCAAGGA   1440
CGAACTTCAT CTATCTAAAG CCAATTCAAT GTCGTATTAT ATGTCTGTTG AAGTCTCCAG   1500
AGTTGTACGG TAGTATCTTG TGTTGAAATG AAGAATGTTG AGTAGTATAG ATCTGTTTTT   1560
AATTGTGGTT TAGAGGTATG TTAAATTTGG AAATTGGTTT CAACGCTAAA ACACTCTTAT   1620
TTGACCTGTT CAGAGAAATA AATCAATATG TAGACAATGA AGGGTTTCTT TTGCTGGTAG   1680
TTTCAAATTT GCCTACTTCA CAGTGATCTA TAAGACTATA AATCTTGCAG GTAGTCAGTT   1740
GCTGAACACA ACATTGGGTG TGAAGGAGTT AGTAGCAAAT GAGTTTGCAA AACTGGAGGA   1800
AGAAGTACTA GTTCCCCACA AGCAACTATT CCCTTTTGAT GTAACTCAAG ATGACTTCTT   1860
TTGGGCATTT GGAATGCTGC GATCAAGAGC ATTCACTTGT CTTGAGGGCC AAAGTCTTGT   1920
TCTAATCCCC TTGGCCGATT TGGTAATCAT CTTTTTCCTT GTTCCTAATT TCATTATAAA   1980
AAAAAAAAAC ATGTACTTTT TCTCATGTTA TGCATTATAC ATGATGAATA TTTATTTAAC   2040
ATGTAAAGTG GGTGCAACAG GCTAACCACA GTCCTGATAT AACAGCACCG AAGTATGCTT   2100
GGGAAATCAG AGGAGCTGGT CTATTCTCTA GAGAACTTGT ATTTTCACTG AGGAATCCAA   2160
CCCCAGTTAA GGCTGGTGAC CAGGTAGTGT TTTTTCTCTC GAATCGAACA ATGAAGTATA   2220
TATAAGTCAC TTAAGTTTAA TGTCAACTGC TACTATCATG GTCCAAGATA CTTAGAATCA   2280
ATAATTCAAC AGGTTCTGAT CCAATACGAT TTGAACAAGA GCAATGCGGA ATTAGCCTTG   2340
GATTATGGGT TGACGGAATC CAGATCAGAA AGAAATGCAT ACACCCTAAC ACTGGAAATA   2400
CCCGAATCAG ATTCTTTTTA CGGGGACAAG CTAGACATAG CTGAGTCAAA TGGGATGGGG   2460
GAAAGTGCCT ACTTTGATAT TGTTTTAGAA CAGCCACTTC CTGCAAATAT GCTACCATAT   2520
TTGAGGCTTG TTGCACTTGG TGGAGAAGAT GCTTTTCTGT TGGAGTCTAT ATTCAGGAAC   2580
TCTATATGGG GACATCTTGA TCTTCCTATT AGCCCTGCCA ATGAGGAGCT CATATGCCAA   2640
GTGATTCGTG ATGCTTGTAC ATCTGCTCTT TCTGGTTACA GTACTACAAT TGCAGAGGTA   2700
ACTCAATATG GTTTTATAGT ATTTGATTTA TCTCTCTTTG TTATAACAAG AATGTGTTGT   2760
TATTTTTTAT TAATGTAGGA TGAGAAGCTG TTAGCAGAAG GTGATATAGA TCCGAGGCTT   2820
GAGATTGCTA TAACTATAAG GTTAGGGGAA AAGAAGGTGT TGCAACAGAT TGATGAGGAA   2880
TTCAAAGAAA GAGAGATGGA ATTGGGTGGT TACGAATACT ACCAAGAACG GAGGCTTAAG   2940
GATCTTGGAT TGGCCGGGGC ACAGGGAGAG AAACTACCCT GGATAGGAGA GGTCTAATTA   3000
TTTATAGAAC ACTTTTCTAC TTGCTTTTCT TTACTTCACT TCACTTCACT TGAGAAAATC   3060
ATTATCCTGA AATTGTAGAA CAATAGTGAT TGATTTTGCT GTAATGTTCA CTTGAAAGTG   3120
GAAACTACAA TCAAAATGCA AACT                                         3144
```

(2) INFORMATION FOR SEQ ID NO: 16:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

```
Met Ala Thr Leu Phe Thr Leu Ile Pro Ser Ser Asn Ser Thr Phe Leu
 1               5                  10                  15

Asn Pro Phe Lys Thr Thr Gln His Ser Lys Leu His Phe Ala Thr Pro
            20                  25                  30

Ser Pro Thr Phe Lys Asn Pro Leu Ser Ile Arg Cys Phe Arg Pro Pro
        35                  40                  45

Glu Thr Asp Thr Pro Pro Glu Ile Gln Lys Phe Trp Gly Trp Leu Ser
 50                  55                  60

Asp Lys Gly Ile Ile Ser Pro Lys Cys Pro Val Lys Pro Gly Ile Val
65                  70                  75                  80

Pro Glu Gly Leu Gly Leu Val Ala Gln Lys Asp Ile Ser Arg Asn Glu
                85                  90                  95

Val Val Leu Glu Val Pro Gln Lys Phe Trp Ile Asn Pro Asp Thr Val
            100                 105                 110

Ala Ala Ser Glu Ile Gly Ser Val Cys Asn Gly Leu Lys Pro Trp Val
        115                 120                 125

Ser Val Ala Leu Phe Leu Met Arg Glu Lys Lys Leu Gly Asn Ser Ser
    130                 135                 140

Ser Trp Lys Pro Tyr Ile Asp Ile Leu Pro Asp Ser Thr Asn Ser Thr
145                 150                 155                 160

Ile Tyr Trp Ser Glu Glu Leu Ser Glu Leu Gln Gly Ser Gln Leu
                165                 170                 175

Leu Asn Thr Thr Leu Gly Val Lys Glu Leu Val Ala Asn Glu Phe Ala
                180                 185                 190

Lys Leu Glu Glu Glu Val Leu Val Pro His Lys Gln Leu Phe Pro Phe
            195                 200                 205

Asp Val Thr Gln Asp Asp Phe Phe Trp Ala Phe Gly Met Leu Arg Ser
        210                 215                 220

Arg Ala Phe Thr Cys Leu Glu Gly Gln Ser Leu Val Leu Ile Pro Leu
225                 230                 235                 240

Ala Asp Leu Trp Val Gln Gln Ala Asn His Ser Pro Asp Ile Thr Ala
                245                 250                 255

Pro Lys Tyr Ala Trp Glu Ile Arg Gly Ala Gly Leu Phe Ser Arg Glu
                260                 265                 270

Leu Val Phe Ser Leu Arg Asn Pro Thr Pro Val Lys Ala Gly Asp Gln
            275                 280                 285

Val Leu Ile Gln Tyr Asp Leu Asn Lys Ser Asn Ala Glu Leu Ala Leu
        290                 295                 300

Asp Tyr Gly Leu Thr Glu Ser Arg Ser Glu Arg Asn Ala Tyr Thr Leu
305                 310                 315                 320

Thr Leu Glu Ile Pro Glu Ser Asp Ser Phe Tyr Gly Asp Lys Leu Asp
                325                 330                 335

Ile Ala Glu Ser Asn Gly Met Gly Glu Ser Ala Tyr Phe Asp Ile Val
                340                 345                 350

Leu Glu Gln Pro Leu Pro Ala Asn Met Leu Pro Tyr Leu Arg Leu Val
```

```
                355                 360                 365
Ala Leu Gly Gly Glu Asp Ala Phe Leu Leu Glu Ser Ile Phe Arg Asn
        370                 375                 380

Ser Ile Trp Gly His Leu Asp Leu Pro Ile Ser Pro Ala Asn Glu Glu
385                 390                 395                 400

Leu Ile Cys Gln Val Ile Arg Asp Ala Cys Thr Ser Ala Leu Ser Gly
                405                 410                 415

Tyr Ser Thr Thr Ile Ala Glu Asp Glu Lys Lys Leu Leu Ala Glu Gly
            420                 425                 430

Asp Ile Asp Pro Arg Leu Glu Ile Ala Ile Thr Ile Arg Leu Gly Glu
            435                 440                 445

Lys Lys Val Leu Gln Gln Ile Asp Glu Glu Phe Lys Glu Arg Glu Met
        450                 455                 460

Glu Leu Gly Gly Tyr Glu Tyr Tyr Gln Glu Arg Arg Leu Lys Asp Leu
465                 470                 475                 480

Gly Leu Ala Gly Ala Gln Gly Glu Lys Leu Pro Trp Ile Gly Glu Val
                485                 490                 495

(2) INFORMATION FOR SEQ ID NO: 17:

(i) SEQUENCE CHARACTERISTICS:
        (A) LENGTH: 492 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

Met Ala Thr Leu Phe Thr Leu Ile Pro Ser Asn Ser Thr Phe Leu
1               5                   10                  15

Asn Pro Phe Lys Thr Thr Gln His Ser Lys Leu His Phe Ala Thr Pro
                20                  25                  30

Ser Pro Thr Phe Lys Asn Pro Leu Ser Ile Arg Cys Phe Arg Pro Pro
            35                  40                  45

Glu Thr Asp Thr Pro Pro Glu Ile Gln Lys Phe Trp Gly Trp Leu Ser
50                  55                  60

Asp Lys Gly Ile Ile Ser Pro Lys Cys Pro Val Lys Pro Gly Ile Val
65                  70                  75                  80

Pro Glu Gly Leu Gly Leu Val Ala Gln Lys Asp Ile Ser Arg Asn Glu
                85                  90                  95

Val Val Leu Glu Val Pro Gln Lys Phe Trp Ile Asn Pro Asp Thr Val
                100                 105                 110

Ala Ala Ser Glu Ile Gly Ser Val Cys Asn Gly Leu Lys Pro Trp Val
            115                 120                 125

Ser Val Ala Leu Phe Leu Met Arg Glu Lys Lys Leu Gly Asn Ser Ser
        130                 135                 140

Ser Trp Lys Pro Tyr Ile Asp Ile Leu Pro Asp Ser Thr Asn Ser Thr
145                 150                 155                 160

Ile Tyr Trp Ser Glu Glu Leu Ser Glu Leu Gln Gly Ser Gln Leu
                165                 170                 175

Leu Asn Thr Thr Leu Gly Val Lys Glu Leu Val Ala Asn Glu Phe Ala
            180                 185                 190

Lys Leu Glu Glu Glu Val Leu Val Pro His Lys Gln Leu Phe Pro Phe
        195                 200                 205

Asp Val Thr Gln Asp Asp Phe Phe Trp Ala Phe Gly Met Leu Arg Ser
```

-continued

```
            210                 215                 220
Arg Ala Phe Thr Cys Leu Glu Gly Gln Ser Leu Val Leu Ile Pro Leu
225                 230                 235                 240

Ala Asp Leu Ala Asn His Ser Pro Asp Ile Thr Ala Pro Lys Tyr Ala
                245                 250                 255

Trp Glu Ile Arg Gly Ala Gly Leu Phe Ser Arg Glu Leu Val Phe Ser
                260                 265                 270

Leu Arg Asn Pro Thr Pro Val Lys Ala Gly Asp Gln Val Leu Ile Gln
                275                 280                 285

Tyr Asp Leu Asn Lys Ser Asn Ala Glu Leu Ala Leu Asp Tyr Gly Leu
                290                 295                 300

Thr Glu Ser Arg Ser Glu Arg Asn Ala Tyr Thr Leu Thr Leu Glu Ile
305                 310                 315                 320

Pro Glu Ser Asp Ser Phe Tyr Gly Asp Lys Leu Asp Ile Ala Glu Ser
                325                 330                 335

Asn Gly Met Gly Glu Ser Ala Tyr Phe Asp Ile Val Leu Glu Gln Pro
                340                 345                 350

Leu Pro Ala Asn Met Leu Pro Tyr Leu Arg Leu Val Ala Leu Gly Gly
                355                 360                 365

Glu Asp Ala Phe Leu Leu Glu Ser Ile Phe Arg Asn Ser Ile Trp Gly
370                 375                 380

His Leu Asp Leu Pro Ile Ser Pro Ala Asn Glu Glu Leu Ile Cys Gln
385                 390                 395                 400

Val Ile Arg Asp Ala Cys Thr Ser Ala Leu Ser Gly Tyr Ser Thr Thr
                405                 410                 415

Ile Ala Glu Asp Glu Lys Lys Leu Leu Ala Glu Gly Asp Ile Asp Pro
                420                 425                 430

Arg Leu Glu Ile Ala Ile Thr Ile Arg Leu Gly Glu Lys Lys Val Leu
                435                 440                 445

Gln Gln Ile Asp Glu Glu Phe Lys Glu Arg Glu Met Glu Leu Gly Gly
                450                 455                 460

Tyr Glu Tyr Tyr Gln Glu Arg Arg Leu Lys Asp Leu Gly Leu Ala Gly
465                 470                 475                 480

Ala Gln Gly Glu Lys Leu Pro Trp Ile Gly Glu Val
                485                 490
```

(2) INFORMATION FOR SEQ ID NO: 18:

(i) SEQUENCE CHARACTERISTICS:
        (A) LENGTH: 495 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Met Ala Thr Leu Phe Thr Leu Ile Pro Ser Ser Asn Ser Thr Phe Leu
1               5                   10                  15

Asn Pro Phe Lys Thr Thr Gln His Ser Lys Leu His Phe Ala Thr Pro
                20                  25                  30

Ser Pro Thr Phe Lys Asn Pro Leu Ser Ile Arg Cys Phe Arg Pro Pro
                35                  40                  45

Glu Thr Asp Thr Pro Pro Glu Ile Gln Lys Phe Trp Gly Trp Leu Ser
                50                  55                  60

Asp Lys Gly Ile Ile Ser Pro Lys Cys Pro Val Lys Pro Gly Ile Val
```

-continued

```
                65                      70                      75                      80
         Pro Glu Gly Leu Gly Leu Val Ala Gln Lys Asp Ile Ser Arg Asn Glu
                              85                      90                      95

Val Val Leu Glu Val Pro Gln Lys Phe Trp Ile Asn Pro Asp Thr Val
                             100                     105                     110

Ala Ala Ser Glu Ile Gly Ser Val Cys Asn Gly Leu Lys Pro Trp Val
                             115                     120                     125

Ser Val Ala Leu Phe Leu Met Arg Glu Lys Lys Leu Gly Asn Ser Ser
                 130                     135                     140

Ser Trp Lys Pro Tyr Ile Asp Ile Leu Pro Asp Ser Thr Asn Ser Thr
         145                     150                     155                     160

Ile Tyr Trp Ser Glu Glu Leu Ser Glu Leu Gln Gly Ser Gln Leu
                             165                     170                     175

Leu Asn Thr Thr Leu Gly Val Lys Glu Leu Val Ala Asn Glu Phe Ala
                             180                     185                     190

Lys Leu Glu Glu Glu Val Leu Val Pro His Lys Gln Leu Phe Pro Phe
                     195                     200                     205

Asp Val Thr Gln Asp Asp Phe Phe Trp Ala Phe Gly Met Leu Arg Ser
                 210                     215                     220

Arg Ala Phe Thr Cys Leu Glu Gly Gln Ser Leu Val Leu Ile Pro Leu
         225                     230                     235                     240

Ala Asp Leu Trp Val Gln Gln Ala Asn His Ser Pro Asp Ile Thr Ala
                             245                     250                     255

Pro Lys Tyr Ala Trp Glu Ile Arg Gly Ala Gly Leu Phe Ser Arg Glu
                             260                     265                     270

Leu Val Phe Ser Leu Arg Asn Pro Thr Pro Val Lys Ala Gly Asp Gln
                     275                     280                     285

Val Leu Ile Gln Tyr Asp Leu Asn Lys Ser Asn Ala Glu Leu Ala Leu
                 290                     295                     300

Asp Tyr Gly Leu Thr Glu Ser Arg Ser Glu Arg Asn Ala Tyr Thr Leu
         305                     310                     315                     320

Thr Leu Glu Ile Pro Glu Ser Asp Ser Phe Tyr Gly Asp Lys Leu Asp
                             325                     330                     335

Ile Ala Glu Ser Asn Gly Met Gly Glu Ser Ala Tyr Phe Asp Ile Val
                             340                     345                     350

Leu Glu Gln Pro Leu Pro Ala Asn Met Leu Pro Tyr Leu Arg Leu Val
                     355                     360                     365

Ala Leu Gly Gly Glu Asp Val Phe Leu Leu Glu Ser Ile Phe Arg Asn
                 370                     375                     380

Ser Ile Trp Gly His Leu Asp Leu Pro Ile Ser Pro Ala Asn Glu Glu
         385                     390                     395                     400

Leu Ile Cys Gln Val Ile Arg Asp Ala Cys Thr Ser Ala Leu Ser Gly
                             405                     410                     415

Tyr Ser Thr Thr Ile Ala Glu Asp Glu Lys Leu Leu Ala Glu Gly Asp
                             420                     425                     430

Ile Asp Pro Arg Leu Glu Ile Ala Ile Thr Ile Arg Leu Gly Glu Lys
                     435                     440                     445

Lys Val Leu Gln Gln Ile Asp Glu Glu Phe Lys Glu Arg Glu Met Glu
                 450                     455                     460

Leu Gly Gly Tyr Glu Tyr Tyr Gln Glu Arg Arg Leu Lys Asp Leu Gly
         465                     470                     475                     480

Leu Ala Gly Glu Gln Gly Glu Lys Leu Pro Trp Ile Gly Glu Val
                             485                     490                     495
```

(2) INFORMATION FOR SEQ ID NO: 19:

(i) SEQUENCE CHARACTERISTICS:
        (A) LENGTH: 491 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Met Ala Thr Leu Phe Thr Leu Ile Pro Ser Asn Ser Thr Phe Leu
1               5                   10                  15

Asn Pro Phe Lys Thr Thr Gln His Ser Lys Leu His Phe Ala Thr Pro
            20                  25                  30

Ser Pro Thr Phe Lys Asn Pro Leu Ser Ile Arg Cys Phe Arg Pro Pro
            35                  40                  45

Glu Thr Asp Thr Pro Pro Glu Ile Gln Lys Phe Trp Gly Trp Leu Ser
        50                  55                  60

Asp Lys Gly Ile Ile Ser Pro Lys Cys Pro Val Lys Pro Gly Ile Val
65                  70                  75                  80

Pro Glu Gly Leu Gly Leu Val Ala Gln Lys Asp Ile Ser Arg Asn Glu
                85                  90                  95

Val Val Leu Glu Val Pro Gln Lys Phe Trp Ile Asn Pro Asp Thr Val
                100                 105                 110

Ala Ala Ser Glu Ile Gly Ser Val Cys Asn Gly Leu Lys Pro Trp Val
            115                 120                 125

Ser Val Ala Leu Phe Leu Met Arg Glu Lys Lys Leu Gly Asn Ser Ser
    130                 135                 140

Ser Trp Lys Pro Tyr Ile Asp Ile Leu Pro Asp Ser Thr Asn Ser Thr
145                 150                 155                 160

Ile Tyr Trp Ser Glu Glu Glu Leu Ser Glu Leu Gln Gly Ser Gln Leu
                165                 170                 175

Leu Asn Thr Thr Leu Gly Val Lys Glu Leu Val Ala Asn Glu Phe Ala
            180                 185                 190

Lys Leu Glu Glu Glu Val Leu Val Pro His Lys Gln Leu Phe Pro Phe
        195                 200                 205

Asp Val Thr Gln Asp Asp Phe Phe Trp Ala Phe Gly Met Leu Arg Ser
    210                 215                 220

Arg Ala Phe Thr Cys Leu Glu Gly Gln Ser Leu Val Leu Ile Pro Leu
225                 230                 235                 240

Ala Asp Leu Ala Asn His Ser Pro Asp Ile Thr Ala Pro Lys Tyr Ala
                245                 250                 255

Trp Glu Ile Arg Gly Ala Gly Leu Phe Ser Arg Glu Leu Val Phe Ser
                260                 265                 270

Leu Arg Asn Pro Thr Pro Val Lys Ala Gly Asp Gln Val Leu Ile Gln
            275                 280                 285

Tyr Asp Leu Asn Lys Ser Asn Ala Glu Leu Ala Leu Asp Tyr Gly Leu
        290                 295                 300

Thr Glu Ser Arg Ser Glu Arg Asn Ala Tyr Thr Leu Thr Leu Glu Ile
305                 310                 315                 320

Pro Glu Ser Asp Ser Phe Tyr Gly Asp Lys Leu Asp Ile Ala Glu Ser
                325                 330                 335

Asn Gly Met Gly Glu Ser Ala Tyr Phe Asp Ile Val Leu Glu Gln Pro
            340                 345                 350
```

Leu Pro Ala Asn Met Leu Pro Tyr Leu Arg Leu Val Ala Leu Gly Gly
            355                 360                 365

Glu Asp Val Phe Leu Leu Glu Ser Ile Phe Arg Asn Ser Ile Trp Gly
    370                 375                 380

His Leu Asp Leu Pro Ile Ser Pro Ala Asn Glu Glu Leu Ile Cys Gln
385                 390                 395                 400

Val Ile Arg Asp Ala Cys Thr Ser Ala Leu Ser Gly Tyr Ser Thr Thr
                405                 410                 415

Ile Ala Glu Asp Glu Lys Leu Leu Ala Glu Gly Asp Ile Asp Pro Arg
                420                 425                 430

Leu Glu Ile Ala Ile Thr Ile Arg Leu Gly Glu Lys Lys Val Leu Gln
            435                 440                 445

Gln Ile Asp Glu Glu Phe Lys Glu Arg Glu Met Glu Leu Gly Gly Tyr
    450                 455                 460

Glu Tyr Tyr Gln Glu Arg Arg Leu Lys Asp Leu Gly Leu Ala Gly Glu
465                 470                 475                 480

Gln Gly Glu Lys Leu Pro Trp Ile Gly Glu Val
                485                 490

(2) INFORMATION FOR SEQ ID NO: 20:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Met Ala Thr Ile Phe Ser Gly Gly Ser Val Ser Pro Phe Leu Phe His
1               5                   10                  15

Thr Asn Lys Gly Thr Ser Phe Thr Pro Lys Ala Pro Ile Leu His Leu
            20                  25                  30

Lys Arg Ser Phe Ser Ala Lys Ser Val Ala Ser Val Gly Thr Glu Pro
        35                  40                  45

Ser Leu Ser Pro Ala Val Gln Thr Phe Trp Lys Trp Leu Gln Glu Glu
    50                  55                  60

Gly Val Ile Thr Ala Lys Thr Pro Val Lys Ala Ser Val Val Thr Glu
65                  70                  75                  80

Gly Leu Gly Leu Val Ala Leu Lys Asp Ile Ser Arg Asn Asp Val Ile
                85                  90                  95

Leu Gln Val Pro Lys Arg Leu Trp Ile Asn Pro Asp Ala Val Ala Ala
            100                 105                 110

Ser Glu Ile Gly Arg Val Cys Ser Glu Leu Lys Pro Trp Leu Ser Val
        115                 120                 125

Ile Leu Phe Leu Ile Arg Glu Arg Ser Arg Glu Asp Ser Val Trp Lys
    130                 135                 140

His Tyr Phe Gly Ile Leu Pro Gln Glu Thr Asp Ser Thr Ile Tyr Trp
145                 150                 155                 160

Ser Glu Glu Glu Leu Gln Glu Leu Gln Gly Ser Gln Leu Leu Lys Thr
                165                 170                 175

Thr Val Ser Val Lys Glu Tyr Val Lys Asn Glu Cys Leu Lys Leu Glu
            180                 185                 190

Gln Glu Ile Ile Leu Pro Asn Lys Arg Leu Phe Pro Asp Pro Val Thr
        195                 200                 205

```
Leu Asp Asp Phe Phe Trp Ala Phe Gly Ile Leu Arg Ser Arg Ala Phe
    210                 215                 220

Ser Arg Leu Arg Asn Glu Asn Leu Val Val Pro Met Ala Asp Leu
225                 230                 235                 240

Ile Asn His Ser Ala Gly Val Thr Thr Glu Asp His Ala Tyr Glu Val
                245                 250                 255

Lys Gly Ala Ala Gly Leu Phe Ser Trp Asp Tyr Leu Phe Ser Leu Lys
            260                 265                 270

Ser Pro Leu Ser Val Lys Ala Gly Glu Gln Val Tyr Ile Gln Tyr Asp
        275                 280                 285

Leu Asn Lys Ser Asn Ala Glu Leu Ala Leu Asp Tyr Gly Phe Ile Glu
    290                 295                 300

Pro Asn Glu Asn Arg His Ala Tyr Thr Leu Thr Leu Glu Ile Ser Glu
305                 310                 315                 320

Ser Asp Pro Phe Phe Asp Asp Lys Leu Asp Val Ala Glu Ser Asn Gly
                325                 330                 335

Phe Ala Gln Thr Ala Tyr Phe Asp Ile Phe Tyr Asn Arg Thr Leu Pro
            340                 345                 350

Pro Gly Leu Leu Pro Tyr Leu Arg Leu Val Ala Leu Gly Gly Thr Asp
        355                 360                 365

Ala Phe Leu Leu Glu Ser Ile Phe Arg Asn Ser Val Trp Gly His Leu
    370                 375                 380

Gly Leu Pro Val Ser Arg Ala Asn Glu Glu Leu Ile Cys Lys Val Val
385                 390                 395                 400

Arg Asp Ala Cys Lys Ser Ala Leu Ser Gly Tyr His Thr Thr Ile Glu
                405                 410                 415

Glu Asp Glu Lys Leu Met Glu Glu Gly Asn Leu Ser Thr Arg Leu Gln
            420                 425                 430

Ile Ala Val Gly Ile Arg Glu Gly Glu Lys Met Val Leu Gln Gln Ile
        435                 440                 445

Asp Gly Ile Phe Glu Gln Lys Glu Leu Glu Leu Asp Gln Leu Glu Tyr
    450                 455                 460

Tyr Gln Glu Arg Arg Leu Lys Asp Leu Gly Leu Cys Gly Glu Asn Gly
465                 470                 475                 480

Asp Ile Leu Gly Asp Leu Gly Lys Phe Phe
                485                 490

(2) INFORMATION FOR SEQ ID NO: 21:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Met Ala Ser Val Phe Ser Val His Pro Leu Pro Ser Ser Ser Phe Leu
1               5                   10                  15

Cys Pro Leu Lys Thr Thr Lys Ser Arg Thr Lys His His Gln Thr Phe
                20                  25                  30

Tyr Thr Tyr Gln Lys Thr Ile Leu Ile Asn Ser Leu Gln Leu Thr Glu
            35                  40                  45

Leu Asp Pro Lys Ile Pro Gln Pro Val Gln Thr Phe Trp Gln Trp Leu
50                  55                  60
```

```
Cys Lys Glu Gly Val Val Thr Thr Lys Thr Pro Val Lys Pro Gly Ile
 65                  70                  75                  80

Val Pro Glu Gly Leu Gly Leu Val Ala Lys Arg Asp Ile Ala Lys Gly
                 85                  90                  95

Glu Thr Val Leu Gln Val Pro Lys Arg Phe Trp Ile Asn Pro Asp Ala
                100                 105                 110

Val Ala Glu Ser Glu Ile Gly Asn Val Cys Ser Gly Leu Lys Pro Trp
            115                 120                 125

Ile Ser Val Ala Leu Phe Leu Leu Arg Glu Lys Trp Arg Asp Asp Ser
    130                 135                 140

Lys Trp Lys Tyr Tyr Met Asp Val Leu Pro Lys Ser Thr Asp Ser Thr
145                 150                 155                 160

Ile Tyr Trp Ser Glu Glu Leu Ser Glu Ile Gln Gly Thr Gln Leu
                165                 170                 175

Leu Ser Thr Thr Met Ser Val Lys Asp Tyr Tyr Gln Asn Glu Phe Gln
                180                 185                 190

Lys Val Glu Glu Val Ile Leu Arg Asn Lys Gln Leu Phe Pro Phe
    195                 200                 205

Pro Ile Thr Leu Asp Asp Phe Phe Trp Ala Phe Gly Ile Leu Arg Ser
    210                 215                 220

Arg Ala Phe Ser Arg Leu Arg Asn Gln Asn Leu Ile Leu Val Pro Phe
225                 230                 235                 240

Ala Asp Leu Thr Asn His Asn Ala Arg Val Thr Thr Glu Asp His Ala
                245                 250                 255

His Glu Val Arg Gly Pro Ala Gly Leu Phe Ser Trp Asp Leu Leu Phe
                260                 265                 270

Ser Leu Arg Ser Pro Leu Lys Leu Lys Ala Gly Asp Gln Leu Phe Ile
    275                 280                 285

Gln Tyr Asp Leu Asn Lys Ser Asn Ala Asp Met Ala Leu Asp Tyr Gly
    290                 295                 300

Phe Ile Glu Pro Ser Ser Ala Arg Asp Ala Phe Thr Leu Thr Leu Glu
305                 310                 315                 320

Ile Ser Glu Ser Asp Glu Phe Tyr Gly Asp Lys Leu Asp Ile Ala Glu
                325                 330                 335

Thr Asn Gly Ile Gly Glu Thr Ala Tyr Phe Asp Ile Lys Ile Gly Gln
                340                 345                 350

Ser Leu Pro Pro Thr Met Ile Pro Tyr Leu Arg Leu Val Ala Leu Gly
    355                 360                 365

Gly Thr Asp Ala Phe Leu Leu Glu Ser Leu Phe Arg Asp Thr Ile Trp
    370                 375                 380

Gly His Leu Glu Leu Ser Val Ser Arg Asp Asn Glu Glu Leu Leu Cys
385                 390                 395                 400

Lys Ala Val Arg Glu Ala Cys Lys Ser Ala Leu Ala Gly Tyr His Thr
                405                 410                 415

Thr Ile Glu Gln Asp Arg Glu Leu Lys Glu Gly Asn Leu Asp Ser Arg
                420                 425                 430

Leu Ala Ile Ala Val Gly Ile Arg Leu Gly Glu Lys Arg Val Leu Lys
            435                 440                 445

Gln Ile Asp Asp Ile Phe Arg Glu Arg Glu Leu Glu Leu Asp Glu Leu
    450                 455                 460

Glu Tyr Tyr Gly Glu Arg Arg Leu Lys Asp Leu Gly Leu Val Gly Glu
465                 470                 475                 480
```

Gln Gly Asp Ile Ile Phe Trp Glu Pro Lys
                485                 490

(2) INFORMATION FOR SEQ ID NO: 22:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TTGGCCGATT TGGTAATCAT CTTTTAACAT GTAAAGTGGG TGCAACAGGC TAACCACAGT    60

(2) INFORMATION FOR SEQ ID NO: 23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

UUGGCCGAUU UGUGGGUGCA ACAGGCUAAC CACAGU                              36

(2) INFORMATION FOR SEQ ID NO: 24:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 24:

Leu Ala Asp Leu Trp Val Gln Gln Ala Asn His Ser
1               5                   10

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

UUGGCCGAUU UGGCUAACCA CAGU                                          24

(2) INFORMATION FOR SEQ ID NO: 26:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
    (ii) MOLECULE TYPE: protein (xi) SEQUENCE DESCRIPTION: SEQ ID NO: 26:

Leu Ala Asp Leu Ala Asn His Ser
1               5
```

ISOLATED SPINACH RIBULOSE-1,5-BISPHOSPHATE CARBOXYLASE/OXGENASE LARGE SUBUNIT ε N-METHYLTRANSFERASE AND METHOD OF INACTIVATING RIBULOSE-1,5-BISHOSPHATASE ε N-METHYLTRANSFERASE ACTIVITY

RELATED APPLICATIONS

This application is a continuation, of application Ser. No. 08/687,916, filed Jul. 29, 1996 now U.S. Pat. No. 5,908,972, which is a CIP of Ser. No. 08/391,000 filed Feb. 21, 1995 now U.S. Pat. No. 5,723,752.

ACKNOWLEDGEMENT OF GOVERNMENT SUPPORT

This invention was made with Government support under Grant No. DE-FG05-92ER26075, awarded by the Department of Energy. The Government may have certain rights in this invention.

BACKGROUND OF THE INVENTION

1. Field of the Invention

This invention relates to ribulose-1,5-bisphosphate carboxylase/oxygenase (Rubisco) large subunit (LS) εN-methyltrnnsferase (protein methylase III or Rubisco LSMT). This enzyme catalyzes methylation of the ε-amine of lysine-14 in the large subunit of Rubisco. Many plant species contain methylated Lys-14 in the LS of Rubisco but some do not (i.e., a des(methyl) lysyl residue in the LS). In addition, the present invention relates to a gene and full-length cDNA clones for Rubisco LSMT. The present invention further relates to transgenic plants and methods of producing same which have the Rubisco LSMT gene inserted into the DNA. This invention also relates to a four amino acid insert (WVQQ) which inactivates the enzymatic activity of Rubisco LSMT and thereby accounts for the subsequent absence of trimethyllysine-14 in the LS of Rubisco.

2. Description of the Related Art

Protein methylation is a widespread and common post-tanslational modification catalyzed by several different protein methyltransferases (Paik et al., "Protein methylation," in Freedman et al. (eds), *The Enzymology of Posttranslational Modifications of Proteins*, vol. 2, pp. 187–228, Academic Press, London (1985)). Proteins which contain trimethyllysyl residues include cytochrome c (Cessay et al., "The relationship between the trimethylation of lysine 77 and cytochrome c metabolism in *Saccharomyces cerevisiae*," *Int. J. Biochem.* 26(5):721–734 (1994); Cessay et al., "Further investigations regarding the role of trimethyllysine for cytochrome c uptake into mitochondria," *Int. J. Biochem.* 23(7,8): 761–768 (1991); DiMaria et al., "Cytochrome c specific methylase from wheat germ," *Biochemistry* 21:1036–1044 (1982); Farooqui et al., "Effect of Methylation on the Stability of Cytochrome c of *Saccharomyces cerevisiae* in vivo," *J. Biol. Chem.* 256(10):5041–5045 (1981); and Farooqui et al., "In vivo studies on yeast cytochrome c methylation in relation to protein synthesis," *J. Biol. Chem.* 255(10):4468–4473 (1980)), calmodulin (Han et al., "Isolation and kinetic characterization of the calmodulin mnethyltransferase from sheep brain," *Biochemistry* 32:13974–13980 (1993); and Rowe et al., "Calmodulin N-methyltransferase," *J. Biol. Chem.* 261 (15):7060–7069 (1986)), histone-H1 (Sarnow et al., "A histone H4-specific methyltransferase properties, specificity and effects on nucleosomal histones," *Biochim. Biophys. Acta* 655:349–358 (1981); and Tuck et al., "Two histone H1-specific protein-lysine N-methyltransferases from *Euglena gracilis*," *J. Biol. Chem.* 260(11):7114–7121 (1985)), and ribosomal proteins (Chang et al., "Purification and properties of a ribosomal protein methylase from *Escherichia coli* Q13," *Biochemisry* 14(22):4994–4998 (1975); Lobet et al., "Partial purification and characterization of the specific protein-lysine N-methyltransferase of YL32, a yeast ribosomal protein," *Biochim. Biophy. Acta* 997:224–231 (1989)). However, the biological function of post-translational protein methylation in all but a few systems remains obscure. Trimethyllysine can serve as a metabolic precursor to carnitine (Paik et al., "Carnitine biosynthesis via protein methylation," *TIBS* 2: 159–162 (1977)), while carboxyl methylation of bacterial membrane proteins plays a major role in chemotaxis (Clarke, "Protein carboxyl methyltransferases: Two distinct classes of enzymes," *Ann. Rev. Biochem.* 54: 479–506 (1985)). Evidence suggests that methylation of Lys-115 in calmodulin affects certain activities including in vitro NAD kinase activation (Roberts et al., "Trimethyllysine and protein function," *J. Biol. Chem.* 261 (4):1491–1494 (1986)), and in vivo susceptibility to ubiquitination (Gregori et al., "Bacterially synthesized vertebrate calmodulin is a specific substrate for ubiquitination," *J. Biol. Chem.* 262(6):2562–2567 (1987); and Gregori et al., "Specific recognition of calmodulin from *Dictyostelium discoideum* by the ATP ubiquitin-dependent degradative pathway," *J. Biol. Chem.* 260(9):5232–5235 (1985); but see also Ziegenhagen et al., "Multiple ubiquitination of calmodulin results in one polyubiquitin chain linked to calmodulin," *FEBS. Lett.* 271(1,2):71–75 (1990); and Ziegenhagen et al., "Plant and fungus calmodulins are polyubiquitinated at a single site in a $Ca^{2+}$-dependent manner," *FEBS Lett.* 273(1,2):253–256 (1990)). Conflicting reports (Farooqui et al., "Effect of Methylation on the Stability of Cytochrome c of *Saccharomyces cerevisiae* in vivo," *J. Biol. Chem.* 256(10):5041–5045 (1981); Frost et al., "Cytochrome c methylation," *Protein methylation*, Ch. 4, pp. 59–76 (1990); and Frost et al., "Effect of enzymatic methylation of cytochrome c on its function and synthesis," *Int. J. Biochem.* 22(10): 1069–1074 (1990); versus Cessay et al., "The relationship between the trimethylation of lysine 77 and cytochrome c metabolism in *Saccharomyces cerevisiae*," *Int. J. Biochem.* 26(5):721–734 (1994); Cessay et al., "Further investigations regarding the role of trimethyllysine for cytochrome c uptake into mitochondria," *Int. J. Biochem.* 23(7,8):761–768 (1991)) also implicate methylation of Lys-77 in cytochrome c as having a role in protein stability, heme incorporation, and mitochondrial transport. A major limitation to elucidating the biological role of lysine methylation in eukaryotes has been the absence of a protein methylase III gene. Hence, molecular studies of the physiological and biochemical function performed by methylation of protein bound lysyl residues have been restricted to site-directed mutational analysis of the methylation site in the target protein (Ceesay et al., "The relationship between the trimethylation of lysine 77 and cytochrome c metabolism in *Saccharomyces cerevisiae*," *Int. J. Biochem.* 26(5) :721–734 (1994); Cessay et al., "Further investigations regarding the role of trimethyllysine for cytochrome c uptake into mitochondria," *Int. J. Biochem.* 23(7,8):761–768 (1991); and Roberts et al., "Expression of a calmodulin methylation mutant affects the growth and development of transgenic tobacco plants," *Proc. Nat. Acad. Sci. USA* 89:8394–8398 (1992)). These studies have been inconclusive as to the exact biological role of methylation of the ε-amine of protein bound lysyl residues.

Ribulose-1,5-bisphosphate carboxylase-oxygenase (Rubisco) catalyzes the reduction of atmospheric $CO_2$ during photosynthesis. A great deal is known about the quaternary structure, catalytic mechanism, active site residues, in vivo regulatory mechanisms, and gene expression for this abundant enzyme, see, for example, Andrews et al., "Rubisco: Structure, Mechanisms, and Prospects for Improvement," in Hatch et al. (eds), *The Biochemistry of Plants*, vol, 10, pp. 131–218. Academic Press, York (1987); Dean et al., "Structure, evolution, and regulation of rbcS genes in higher plants," *Annu. Rev. Plant. Physiol. Plant Mol. Biol.* 40: 415–439 (1989); and Mullet, "Chloroplast development and gene expression," *Annu. Rev. Plant. Physiol. Plant Mol. Biol.* 39: 475–502 (1988). Higher plant Rubisco is a hexadecameric protein composed of eight chloroplast-encoded large subunits (referred to herein as "LS") and eight nuclear-encoded small subunits (referred to herein as "SS"). Synthesis of the LS is accompanied by post-translational processing of the N-terminal domain (Houtz et al., "Post-translational modifications in the large subunit of ribulose bisphosphate carboxylase/oxygenase," *Proc. Natl. Acad. Sci. USA* 86:1855–1859 (1989); and Mulligan et al., "Reaction-intermediate analogue binding by ribulose bisphosphate carboxylase/oxygenase causes specific changes in proteolytic sensitivity: The amino-terminal residue of the large subunit is acetylated proline," *Proc. Natl. Acad. Sci. USA* 85:1513–1517 (1988)). The N-terminal Met-1 and Ser-2 are removed and Pro-3 acetylated. Additionally, the LS of Rubisco from tobacco, muskmelon, pea, and several other species is post-translationally modified by trimethylation of the ε-amine of Lys-14 (Houtz et al., "Posttranslational modifications in the amino-terminal region of the large subunit of ribulose-1,5-bisphosphate carboxylase/oxygenase from several plant species," "*Plant Physiol.* 98:1170–1174 (1992); Houtz et al., "Post-translational modifications in the large subunit of ribulose bisphosphate carboxylase/oxygenase," *Proc. Natl. Acad. Sci. USA* 86:1855–1859 (1989)). The enzyme responsible for this latter modification is a highly specific chloroplast-localized S-adenosylmethionine (AdoMet):protein (lys) εN-methyltransferase (protein methylase III, Rubisco LSMT, EC 2.1.1.43) (Houtz et al., "Post-translational modifications in the large subunit of ribulose bisphosphate carboxylase/oxygenase," *Proc. Natl. Acad. Sci. USA* 86:1855–1859 (1989)).

Rubisco LSMT has been affinty purified ~8000-fold from pea chloroplasts and identified as a monomeric protein with a molecular mass of ~57 kDa (Wang et al., "Affinity Purification of Ribulose-1,5-bisphosphate Carboxylase/Oxygenase Large Subunit εN-Methyltransferase," accepted by *Protein Expression and Purification* (1995)). Recently, Rubisco LSMT cDNAs have been cloned and sequenced from pea and tobacco (Klein et al., "Cloning and developmental expression of pea ribulose-1,5-bisphosphate carboxylase/oxygenase large subunit N-methyltransferase," *Plant Molecular Biol.* 27:249–261 (1995); Ying et a l., "Organization and characterization of the ribulose-1,5-bisphosphate carboxylase/oxygenase large subunit εN-methyltransferase gene in tobacco," *Plant Molecular Biology* (In press)). The deduced amino acid sequences of tobacco Rubisco LSMT has 64.5% identity and 75.3% similarity with the sequence of pea Rubisco LSMT, and both pro teins contain several copies of a conserved imperfect leucine-rich repeat motifs (Ying et al., "Organization and characterization of the ribulose-1,5-bisphosphate carboxylase/oxygenase large subunit εN-methyltransferase gene in tobacco," *Plant Molecular Biology* (In press)).

Rubisco LSMT has high specific specificity, methylating only Rubisco and only lysyl residue 14 in the LS. Of many plant species examined several contain methylated Lys-14 in the LS of Rubisco, such as pea and tobacco, but some do not, such as spinach and alfalfa (ooutz et al., "Post-translational modifications in the large subunit of ribulose bisphosphate carboxylase/oxygenase," *Proc. Natl. Acad. Sci. USA* 86:1855–1859 (1989); Houtz et al., "Posttranslational modifications in the amino-erminal region of the large subunit of ribulose-1,5-bisphosphate carboxylase/oxygenase from several plant species," *Plant Physiol.* 98:1170–1174 (1992); and unpublished data). There has been no explanation for the existence of Lys-14 in the LS of Rubisco in a non-methylated state (i.e., a des(methyl) lysyl residue in the LS). Further, since some plant species, such as spinach, wheat, corn (maize) and lettuce do not contain methylated Lys-14 in the LS of Rubisco (Houtz et al. "Posttranslational modifications in the amino-terminal region of the large subunit of ribulose-1,5-bisphosphate carboxylase/oxygenase from several plant species," *Plant Phtysiol.* 98:1170–1174 (1992); and unpublished data), it was once assumed that these same plant species did not possess the Rubisco LSMT gene.

SUMMARY OF THE INVENTION

In view of the state of the art as previously described, there thus exists a need in the art for a better understanding of post-translational protein methylation in plants. More specifically, a better understanding for the molecular basis for the absence of trimethylation-14 in the LS of Rubisco from certain plant species.

It is thus an object of the present invention to provide a Rubisco LSMT gene.

It is a further object of the present invention to provide the DNA and amino acid sequence for a Rubisco LSMT enzyme.

It is a still further object of the present invention to provide full-length cDNA clones for Rubisco LSMT.

In a first aspect, the present invention relates to a Rubisco LSMT gene which exists in a higher plant with a des (methyl) lysyl residue in the LS of Rubisco. A particularly preferred higher plant includes the spinach plant.

In a second aspect, the present invention relates to the DNA and amino acid sequence for a Rubisco LSMT enzyme.

In a third aspect, the present invention relates to a recombinant vector including the Rubisco LSMT gene described above. The vector is suitable for transforming higher plants.

In a fourth aspect, the present invention relates to an isolated or recombinant Rubisco LSMT enzyme encoded by the Rubisco LSiNIT gene described above.

In a fifth aspect, the present invention relates to a recombinant or transgenic plant transformed with the Rubisco LSMT gene described above.

In a sixth aspect, the present invention relates to a method of inactivating Rubisco LSMT activity which comprises inserting a 4 amino acid sequence [SEQ ID NO:1] insert (WVQQ) into Rubisco LSMT.

In a further aspect, the present invention relates to a method for preventing or reducing Rubisco LSMT activity in a photosynthesizing plant comprising transforming a photosynthesizing plant with a recombinant vector wherein the vector comprises a Rubisco LSMT gene with the 12 nucleotide insert.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIGS. 2A–2F [SEQ ID NOS: 15–17] shows the nucleotide sequence of the rbcMT-S and the corresponding deduced amino acid sequences. Introns are printed in lower case letters and exons in upper case letters. The putative start and stop codons are underlined. The 12 nucleotides and corresponding 4 amino acids representing the auxon sequence are indicated by bold italic letters. The deduced polypeptide for the S38 cDNA is underneath the one for the S40 cDNA that contains the auxon. The oligonucleotide primers for sequencing, PCR and RACE, are indicated by arrows above the nucleotide sequence. The primers labeled with a star are derived from the conserved regions of pea and tobacco Rubisco LSMTs.

FIGS. 3A–3C [SEQ ID NOS: 18–21] is a comparison of the deduced amino acid sequences of S38, S40, with tobacco and pea Rubisco LSMTs. Identical residues are indicated by vertical lines and similar residues by colons. Gaps introduced to maximize alignment are indicated by dashes. Potential N-glycosylation sites are shown in bold. Leucine-rich repeat-like motifs are underlined. The four amino acid sequence, WVQQ, deduced from the 12-nt auxon is shown in bold italic letters. The conserved peptide sequences, from which the primers are derived to clone the rbcMT-S, are indicated by arrows.

DETAILED DESCRIPTION OF THE INVNTION

Figure 1A:
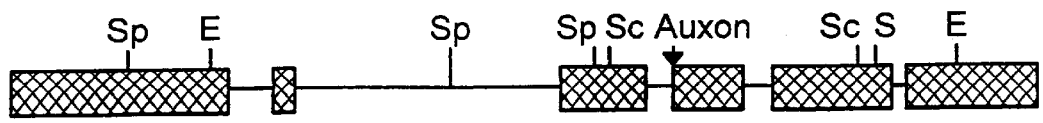
FIG. 1A illustrates the genornic organization and restriction map of rbcMT-S. Exons are shown as heavy black bars, introns as horizontal lines, and the auxon is indicated by an arrow.

The present invention relates to a Rubisco LSMT gene, its DNA and amino acid sequence encoding therefor, cDNA clones thereof, and a four amino acid sequence insert which inactivates the enzymatic activity of Rubisco LSMT.

In the present application, naturally occurring amino acid residues in peptides are abbreviated as recommended by the IUPAC OIUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr of Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly o r G, and X is any amino acid.

Synthetic or non-naturally occurring amino acids refer to amino acids which do not naturally occur in vivo but which, nevertheless, can be incorporated into the peptide structures described herein. Preferred synthetic amino acids are the D-amino acids of naturally occurring L-amino acids as well as non-nturally occurring D and L amino acids represented by the formula $H_2NCHR^1COOH$, wherein $R^1$ is: (1) a lo wer alkyl group; (2) a cycloalkyl group of from 3 to 7 carbon atoms; (3) a heterocycle of from 3 to 7 carbon atoms and 1 to 2 heteroatoms selected from the group consisting of oxygen, sulfur, and nitrogen; (4) an aromatic or arylalkyl residue of from 6 to 15 carbon atoms optionally having from 1 to 3 substituents on the aromatic nucleus selected from the group consisting of hydroxyl, lower alkoxy, amino, and carboxyl; (5) alkylene-Y where alkylene is an alkylene group of from 1 to 7 carbon atoms and Y is selected from the group consisting of hydroxy, amino, cycloalkyl of from 3 to 7 carbon atoms, heterocyclic of from 3 to 7 carbon atoms and 1 to 2 heteroatoms selected from the group consisting of oxygen, sulfur and nitrogen, and $—C(O)R^2$ where $R^2$ is selected from the group consisting of hydrogen, lower alkyl, lower alkoxy, and $—NR^3R^4$ where $R^3$ and $R^4$ are independently selected from the group consisting of hydrogen and lower alkyl; (6) alkylene-$S(O)_nR^5$ where n is 1 or 2, and $R^5$ is a lower alkyl or lower alkylene.

Particularly preferred synthetic amino acids include, by way of example, the D-amino acids of naturally occurring L-amino acids, L-1-napthylalanine, L-2-naphthylalanine, L-cyclohexylalanine, L-2-amino isobutyric acid, the sulfoxide and sulfone derivatives of methionine, and the lower alkoxy derivatives of methionine.

"Peptide mimetics" are also encompassed by the present invention and include peptides having one or more of the following modifications:

peptides wherein one or more of the peptidyl [—C(O)NH—] linkages (bonds) have been replaced by a non-peptidyl linkage such as carbamate linkage [—OC(O)N<], phosphonate linkage, amidate linkage, sulfonamide linkage, and secondary amine linkage or with an alkylated peptidyl linkage [C(O)NR$^6$- where R$^6$ is a lower alkyl], peptides wherein the N-terminus is derivatized to a —NR$^7$R$^8$ group, to a —NC(O)R$^7$ group where R$^7$ and R$^8$ are independently selected from hydrogen and lower alkyls with the proviso that R$^7$ and R$^8$ are both not hydrogen, to a succinimide group, to a benzyloxycarbonyl-NH-(CBZ-NH-) group, to a benzyloxycarbonyl-NH- group having from 1 to 3 substituents on the phenyl ring selected from the group consisting of lower alkyl, lower alkoxy, chloro, and bromo, peptides wherein the C terminus is derivatized to >C(O)R$^9$ where R$^9$ is selected from the group consisting of hydrogen, lower alkyl, lower alkoxy, and NR$^{10}$OR$^{11}$ where R$^{10}$ and R$^{11}$ are independently selected from the group consisting of hydrogen and lower alkyl.

Other abbreviations are as follows: aa, amino acid(s); auxon, auxiliary exon; bp, base pair(s); nt, nucleotide(s); Rubisco LSMT, Ribulose-1,5-bisphosphate carboxylase/oxygenase large subunit $^\epsilon$N-methyltransferase; RACE, rapid amplification of cDNA ends; RT-PCR, reverse transcription-polymerase chain reaction Although the present invention is described with respect to spinach, it will be appreciated that the techniques employed herein are applicable to other plants species which contain a des(methyl) form of Rubisco with regards to trimethylation of lysyl residue 14 in the large subunit (LS). Examples of such plant species include alfalfa, wheat, corn (maize) and lettuce.

Ribulose-1,5-bisphosphate carboxylase/oxygenase (Rubisco) large subunit (LS) $^\epsilon$N-methyltransferase (referred to herein as "Rubisco LSMT") catalyzes methylation of the $\epsilon$-amine of lysine-14 in the LS of Rubisco. Rubisco is the world's most abundant protein, and serves as the only significant link between the inorganic and organic carbon pools in the Earth's biosphere by catalyzing the reduction of atmospheric carbon dioxide to carbohydrates during photosynthesis. Perturbations of Rubisco activity translate directly into similar changes in plant growth and yield. Thus, there is significant interest in the art in the potential manipulation and control of Rubisco activity through genetic engineering.

However, the complexity and multimeric nature of Rubisco have proven to be substantial obstacles to achieving this goal, which have not yet been overcome. Rubisco LSMT provides an opportunity for the selective manipulation of Rubisco activity through changes in the structure and stability of the N-terminal region in the LS, an area known to be essential for catalytic activity. Rubisco LSMT is a highly specific enzyme which is found to interact only with Rubisco and does not interact with any other protein in the plant cell. Since Rubisco catalyzes the reduction of atmospheric $CO_2$ during photosynthesis, Rubisco and Rubisco LSMT are critical to the plant cell for viability. Furthermore, the exceptionally tight and specific nature of the interaction between Rubisco LSMT and des(methyl) forms of Rubisco creates the possibility for the development of novel synthetic polypeptide herbicides, whose target is the in vivo interaction between Rubisco LSMT and Rubisco, whose specificity crosses a group of plant species related only by the presence of Rubisco LSMT, and whose target protein has no homologue in the entire animal kingdom. Finally, this same affinity of Rubisco LSMT for des(methyl) forms of Rubisco also creates the possibility for the site and protein specific delivery of compounds into the chloroplast and to Rubisco, for the potential manipulation of Rubisco activity and/or stability.

Ribulose bisphosphate carboxylase/oxygenase (Rubisco) from spinach (Spinach oleracea) is a des(methyl) form of Rubisco with regards to trimethylation of lysyl residue 14 in the large subunit (Ls). In investigating the molecular basis for the absence of trimethylation-14 in the LS of spinach Rubisco, the inventor has isolated and sequenced two full-length cDNAs (S40 and S38) and the gene for spinach Rubisco LSMT (rbcMT-S). This discovery was quite unexpected since it was once thought that spinach did not possess the Rubisco LSMT gene because it contained a des(methyl) lysyl residue in the LS of Rubisco. The gene for spinach Rubisco LSMT, covering all 6 exons and 5 introns, has an organization similar to the tobacco Rubisco LSMT gene (rbcMT-T). Southern blot analysis of spinach genomic DNA shows that the rbcMT-S is present as a single copy. The deduced amino acid sequence from the rbcMT-S cDNAs shows 60% and 62% identity with the amino acid sequences of pea and tobacco Rubisco LSMT, respectively.

Moreover, the particular sequence disclosed herein for the spinach Rubisco LSMT gene may be used to determine the particular sequence in other photosynthesizing plants. The sequence of the gene may be used as a probe to screen cDNA or genomic DNA libraries from other plants and, due to the expected homology between the gene sequences the various plant species, the particular sequence for the Rubisco LSMT gene in other species may then be found.

In a further aspect, the present invention relates to a recombinant or transgenic plant transformed with the Rubisco LSMT gene described above. The methods employed for transforming the plants are generally known in the art. For example, the transformation method described in Bechtold et al, *Planta Agrobacterium Mediated Gene Transfer By Infiltration of Adult Arabidopsis Thaliana Plants*, C. R. Acad. Sci., Paris 316:1194–1199 (1993) and Valvekens et al, "*Agrobacterium tumefaciens*-mediated transformation of *Arabidopsis thaliana* root explants by using kanamycin selection," Proc. Natl. Acad. Sci. USA 85:5536–5540 (1988), may be used in the method of the present invention.

To achieve the present invention, a full-length cDNA clone was isolated by the present inventor utilizing polymerase chain reaction (PCR)-based technology and conventional bacteriophage library screening. CR techniques are disclosed, for example, in Klein et al, "Cloning and Developmental Expression of the Sucrose-Phosphate-Synthase Gene From Spinach," *Planta* 190:498–510 (1993); in Ampli-Taq PCR kit by Perkin Elmer - Cetus, Emeryville, Calif.); and in the manufacturer's instruction manual. Bacteriophage library screening is described, for example, in Gantt et al, "Transfer of rp122 to the Nucleus Greatly Preceded its loss from the Chloroplast and Involved the Gain of an Intron," *EMBO J.* 10:3073–3078 (1991), and in the information provided by the manufacturer of the screening membrane (Stratagene, La Jolla, Calif.).

A cDNA of the Rubisco LSMT gene from spinach was isolated and studies of Rubisco LSMT gene expression initiated. Utilizing amino acid sequence information derived from purified peptic polypeptide fragments from proteolyzed Rubisco LSMT, a full-length cDNA of Rubisco LSMT was obtained. The cDNA of Rubisco LSMT, rbcMT, was used to examine organ-specific and developmental parameters affecting rbcMT gene expression.

The present specification details the purification of peptic fragments from spinach Rubisco LSMT and a PCR-based cloning strategy for isolating a full-length cDNA. A similar strategy was previously utilized to obtain a full-length cDNA of sucrose-phosphate synthase from spinach (Klein et al, "Cloning and developmental expression of the sucrose-phosphate-synthase gene from spinach," *Planta.* 190:498–510 (1993)) and to obtain the cDNA of the Rubisco LSMT gene from pea and from tobacco. The protein sequence information obtained from peptic fragments permitted the confirmation of clones encoding for Rubisco LSMT. Hence, a molecular probe of the spinach Rubisco LSMT gene was rapidly obtained thereby permitting identification of protein and nucleotide sequence, and characterization of its gene expression.

Figure 2F:
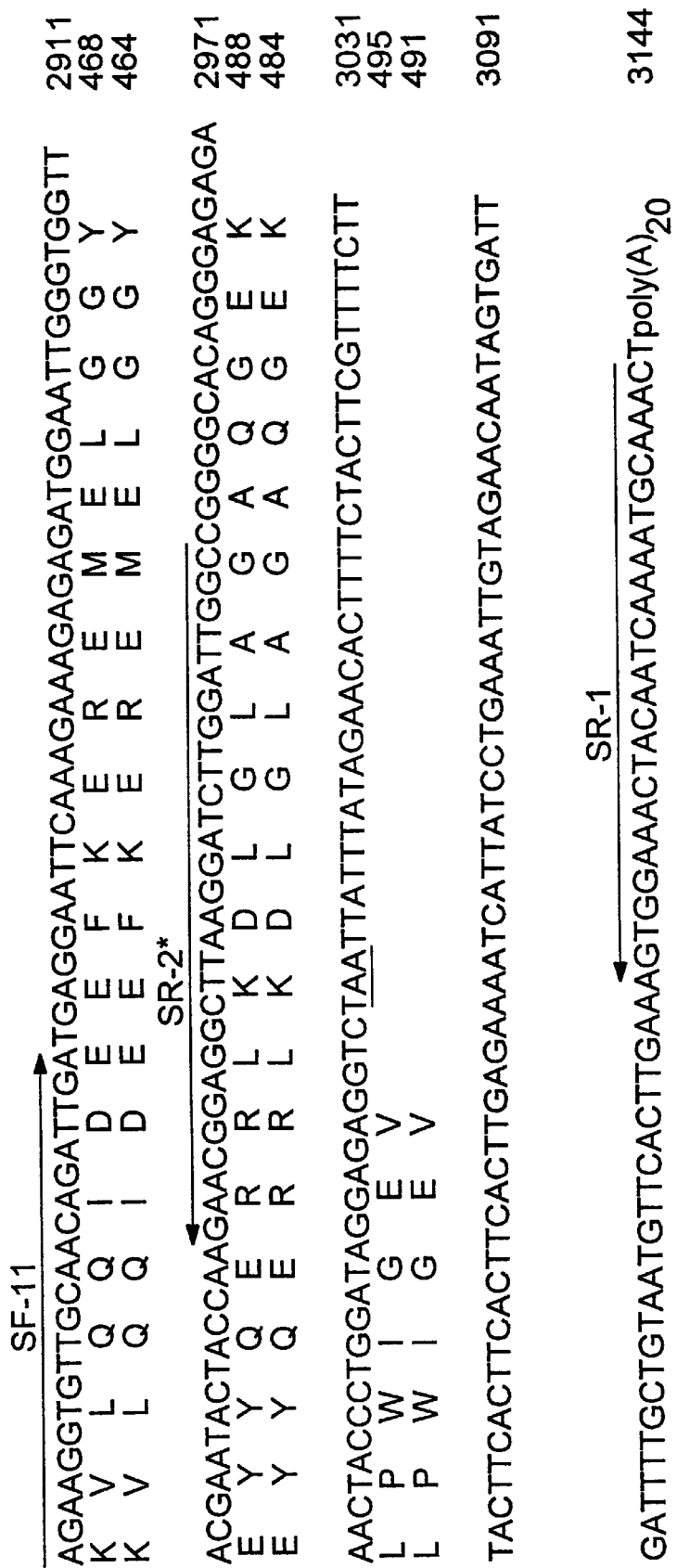
Figure 4:
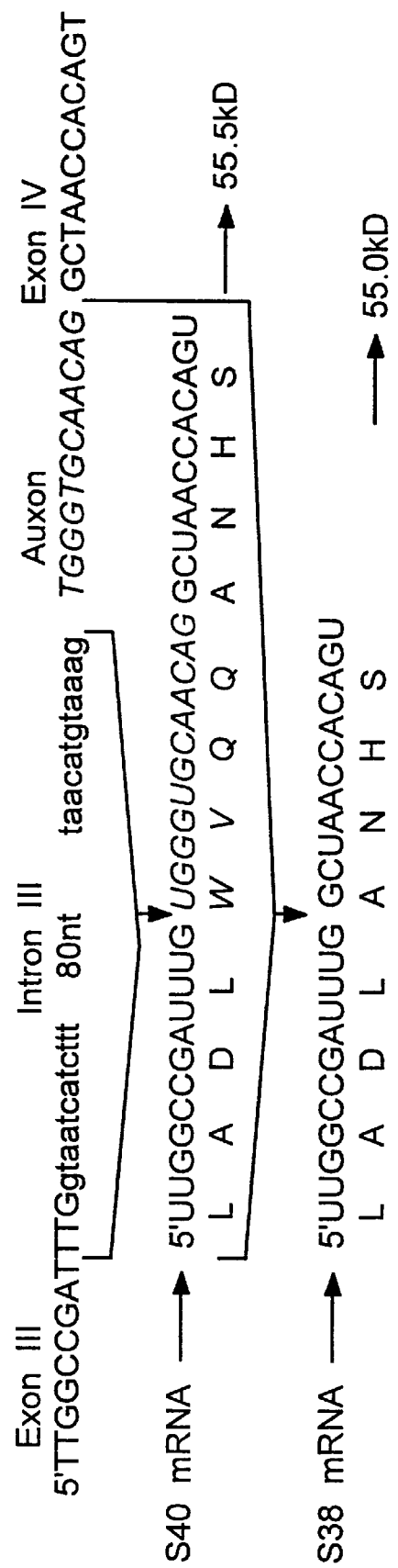
FIG. 4 [SEQ ID NOS: 22–26] illustrates alternative splicing of intron M of rbcMT-S mRNA. The top portion shows the sequence of intron III and flanking regions. Shown below are the two types of mRNAs (S40 and S38) produced by alternative splicing. When the second 3' splice site is utilized, the 12-nt auxon is retained to produce S40 mRNA (center), which encodes a 55.5 kD polypeptide. If the first 3' splice site is utilized, the auxon is absent and S38 mRNA is produced (bottom), which encodes a 55.0 kD polypeptide.

The amino acid sequence deduced from the S40 cDNA, as described in the Examples and in FIGS. 2, 3 and 4, contains a 4-amino acid [SEQ ID NO:1] insert (WVQQ) located near the center of the protein, which is a consequence of alternative 3' mRNA splicing and inclusion of 12 nucleotides from the 3' end of intron III. For example, the 4-amino acid sequence was determined to be a 12 nucleotide [SEQ ID NO.:2] insert (TGGGTGCAACAG). Bacterial expression of the S40 cDNA using a pET expression vector resulted in the synthesis of a protein with no detectable activity. Furthermore, engineering of the 4-amino acid insert from the S40 cDNA into the corresponding position in pea Rubisco LSMT resulted in a complete loss of enzyme activity. This technique of inserting the 4-amino acid insert to inactivate the LSMT could also be used in other species having Rubisco LSMT, for example, in tobacco, tomato, potato, pepper, legumes, soy beans, cucumbers, melons and gourds. The methods employed for inserting the 4-amino acid insert into the Rubisco LSMT are generally known in the art. The alternative 3' mRNA splicing, therefore, resulted in the inactivation of the S40 LSMT. This is one molecular rationale for the absence of trimethyllysine-14 in the LS of spinach Rubisco.

Catalytically inactivated forms of Rubisco LSMT can act as competitive ligands to prevent or reduce methylation at Lys-14. Therefore, transgenic plants can be constructed which carry full-length copies of the Rubisco LSMT with the 4-amino acid insert. Since the Rubisco LSMT enzyme is essential for Rubisco activity, the down-regulation the enzyme's activity would be expected to be lethal to the plant since it would be unable to catalyze net $CO_2$ fixation during photosynthesis. Accordingly, the present invention provides a method for preventing or reducing Rubisco ISMT activity in a photosynthesizing plant. This method, and variations of this method, could thus be used as a herbicide to selectively eliminate or reduce photosynthesizing plants.

The following examples are presented in order to more fully illustrate the preferred embodiments of the invention. They should in no way be construed, however, as limiting the broad scope of the invention.

EXAMPLES

Example 1

Plant growth

Spinach (*Spinacea oleracea* L. cv. Melody) plants were cultured in ProMix™ soil media in a greenhouse at approximately 20° C. with a naliral light photoperiod during the winter season (Lexington, Ky.).

Example 2

Cloning and sequencing of rbcMT-S cDNAs

Figure 1B:
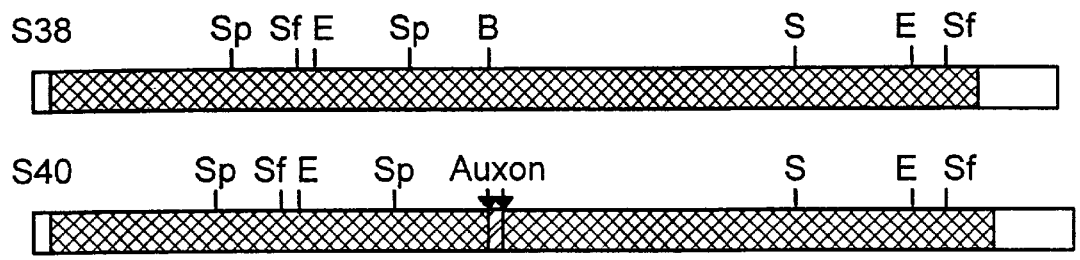
FIG. 1B is a diagrammatic representation of the S38 and S40 cDNAs with coding regions as heavy black bars, untranslated regions as open bars and the auxon as a shaded bar.

The two rbcMT-S cDNAs were obtained by RT-PCR (reverse transcription-polymerase chain reaction) and RACE (rapid amplification of cDNA ends). For RT-PCR, 5 μg of total RNA isolated from spinach leaves using Trizol (GIBCO/BRL) was reverse-transcribed with an oligo $d(T)_{17}$ primer. The resulting first-strand cDNA product was amplified by PCR with Taq polymerase (GIBCO/BRL) using a forward primer (SP-8), and a reverse primer (SR-2). The SF-8 and SR-2 primers were synthesized corresponding to conserved peptide sequences between pea (Klein et al., "Cloning and developmental expression of pea ribulose-1, 5-bisphosphate carboxylase/oxygenase large subunit N-methyltransferase," *Plant Molecular Biol.* 27:249–261 (1995)) and tobacco (Ying et al., "Organization and characterization of the ribulose-1,5-bisphosphate carboxylase/oxygenase large subunit εN-methyltransferase gene in tobacco," *Plant Molecular Biology* (In press)) Rubisco LSMTS. The SF-8 sequence [SEQ ID NO: 4], including an EcoRI site and encoding the peptide [SEQ ID NO.:3] WAFGILRSRA, is 5'CGA TGG GCA TIT GGA ATT CTC AGA TCA AGG GC. The SR-2 sequence [SEQ ID NO.:6], including a Bg/II site and encoding the peptide [SEQ ID NO.: 5] ERRLKDLGLA, is 5'GGC CAA GGC CAA GAT CTT TAA GCC TCC TTT C. Conditions for PCR were 35 cycles of: 94° C. 1 min, 50° C. 1 min, 72° C. 1.5 min and final extension 72° C. 10 min. The PCR product was digested with EcoRI and Bg/II, and gel-purified. The purified fragment was cloned into Bluescript 11 KS(+) vector (Stratagene) for sequencing. After sequencing, this clone was designated as S25' (FIG. 1D).

For 5'RACE, reverse-transcription was the same as described above except for using an rbcMT-S-specific primer (SR-3, FIG. 2) anchored in the mid-coding region and followed by poly d(C)-tailing as described in Ying et al., "Isolation and characterization of xnov, a *Xenopus laevis* ortholog of the chicken nov gene," *Gene* 171:243–248 (1996)). The resulting dC-tailed products were amplified using a nested primer (SR-5) which included a XbaI restriction site. and a poly (dG/dI)-containing oligonucleotide [SEQ ID NO.:7] (AP-2, 5'GCT AAG CTT CTA GAG CTC GGI IGG GII GGG IIG G, SacI). The PCR products were digested with ScaI and XDaI, gel-purified and cloned into Bluescript II KS(+) vector for sequencing. After sequencing, two different clones were identified, one with a 12-bp auxiliary exon (auxon) designated as S40' and another without the auxon designated as S38'.

For 3'RACE, 5 μg of total RNA from spinach leaves was reverse-transcribed with an adapter-primer [SEQ ID NO.:8] (AP-1,5'GGC CAC GCG TCG ACT AGT ACT $(T)_{16}$). Amplification by PCR was as described above except for using the AP-1 and spinach specific primer (SF-9). The PCR product was cloned into pCR-Scrip Direct SK(+) vector (Stratagene) for sequencing, designated as S2' (FIG. 1D).

Two to five independent clones were chosen for sequencing from each of the above constructs. Both strands of each clone were sequenced by the dideoxy chain termination method (Sanger et al., "DNA sequencing with chain-terminating inhibitors," *Proc. Natl. Acad. Sci. USA* 74:5463–5467 (1977)) using Sequenase (US Biochemical) and $^{35}$S-DATP (NEN) with M13 reverse and -40 primers. In addition, 18 to 27-mer oligonucleotides synthesized according to sequence information obtained were used directly as primers for further sequencing.

Both full-length S38 and S40 cDNAs were obtained by ligation of clones S2' and S25' to S38' and S40', accordingly, based on restriction sites within the overlapped regions (FIG. 1D).

Example 3
Isolation and Southern analysis of the rbcMT-S

The rbcMT-S gene was cloned by PCR. Spinach nuclear DNA was isolated using Floraclean (Bio101, Inc.). Approximately 100 ng of the nuclear DNA was amplified by PCR with Tac polymerase (GIBCO/BRL) using a forward primer (SF-1) and a reverse primer (SR-1). The PCR product was cloned into pCR-Script SK(+) for sequencing and restriction mapping.

For Southern analysis, spinach nuclear DNA was digested with EcoRI or ScaI, electrophoresed on a 0.7% agarose gel and transferred onto nylon membranes (MSI) (Sambrook et al., *Molecular Cloning: A Laboratory Manual* (Cold Spring Harbor Lab., Cold Spring Harbor, N.Y.), 2nd Ed. (1989)). The DNA blot was hybridized with the cDNA probe I (SfrI fragment, 1056-bp long, FIG. 1C) labeled with digoxigenin-UTP according to the procedure provided by the manufacturer (Boehringer Mannheim).

Example 4
Genetic engineering of the (12-bp) auon into the pea LSMT

A 5'end-truncated pea LSMT cDNA cloned in pET-23d (P-55) (Cheng and Houtz, unpublished data) was digested with KpnI which generated a 802-bp fragment I and a 4300-bp fragment H which were gel-purified. The purified 802-bp fragment was self-ligated and then amplified by Taq polymerase with a forward primer [SEQ ID NO.: 9] (P-F, 5'AGT CCC GGG TGC AAC AGA TTA ACC ACA GTG CAG GAG TTA C, SmaI. Note: 12 nucleotides, including one in the reverse primer, are in bold italic letters and consist of the auxon) and a reverse primer [SEQ ID NO.:10] (P-R, 5'AGT TTT AAA GGT CTG CCA TTG GAA CCA C, DraI) at 35 cycles of: 94° C. 1 min, 56° C. 1 min, 72° C. 40 sec and final extension 72° C. 10 min. The PCR product was digested with SmaI and DraI, and self-religated. The circular DNA was digested with KpnI, ligated into KpnI-fragment I, and transformed into DH5α cells (BRL/GIBCO). After screening 180 colonies, two of them (designated as P-55–84, and P-55–174) were selected for sequencing to confirm that the 12-bp auxon was engineered into the P-55 and no other mutation was caused by PCR. The full-length encoding regions of S40 and S38 cDNA were also cloned into the pET-23d *E. coli* expression vector (designated as S-40 and S-38 respectively).

Example 5
RNase protection assay

Figure 1C:
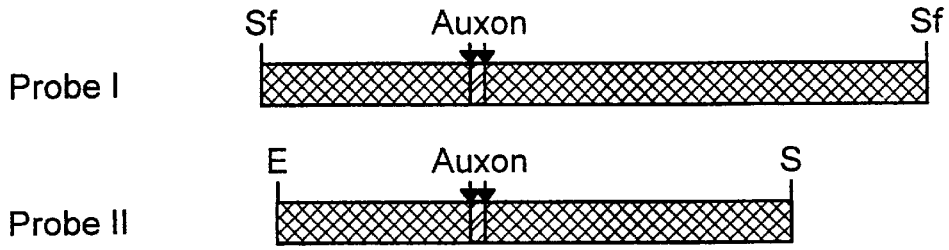
FIG. 1C shows Probe I, which is a 1056-bp SfrI fragment with the 12-bp auxon, and Probe II, which is a riboprobe for the RNAase protection assay which results in only one 775-nt fragment protected by S40 mRNA, and two 306-nt and 457-nt fragments protected by S38 mRNA.
Figure 1D:
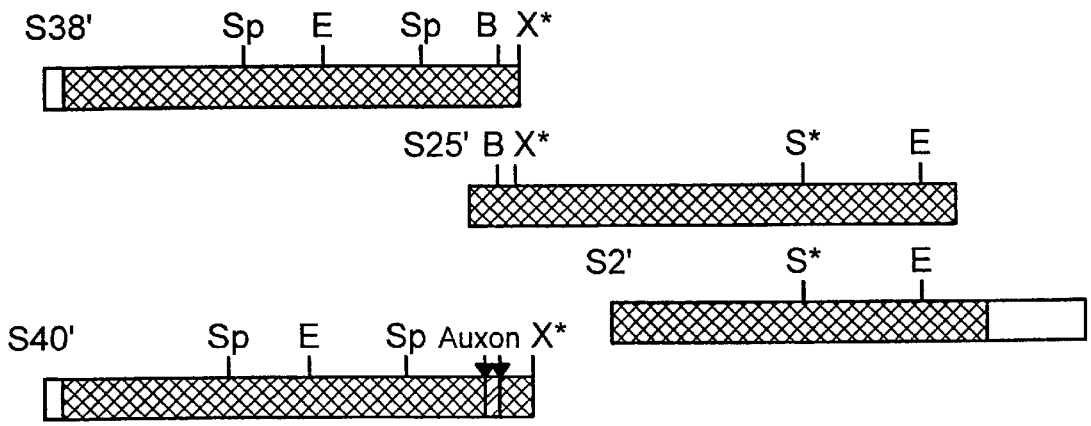
FIG. 1D depicts the strategy for PCR cloning and joining different cDNA fragments. The restriction enzymes labeled with stars were used to ligate corresponding fragments. Abbreviations for restriction sites: B, BglI; E, EcoRI; S, SacI; Sc, ScaI; Sf, SfrI; Sp, SpeI and X, XbaI.

The antisense riboprobe (probe II) was made by transcribing a rbcMT-S cDNA clone 210–1 (which contained a 775-bp EcoRI-SacI fragment with the 12-bp auxon and was linearized by EcoRI, FIG. 1C) with T7 RNA polymerase, ($\alpha$-$^{32}$P)UTP (800 Ci/mmol, 10 mCi/ml) and cold NTP. Probe III generated a 775-nt which was fully protected by the S40 mRNA but only partially protected by the S38 mRNA. The 2.5, 5, 10, 20 and 20 μg of total RNA isolated from spinach leaves were hybridized with 1×10$^5$ cpm of the probe II according to the manufacturer's instructions (Ambion).

Example 6
Rubisco LSMT activity assay and western blot analysis

Individual clones (S40, S-38, P-55 and P-55–174) in pLysS host cells were cultured at 37° C. for 3.5 hrs in 5 ml LB broth with 50 μg/ml carbenicillin and 35 μg/ml chlorophenicol and induced by the addition of IPTG to the growing cells at a final concentration of 0.5 mM. After induction cell cultures were continued for 2.5 hrs at 25° C. After induction the cells were harvested by centrifugation at 5000× g for 5 min at 4° C., washed twice with deionized water, and resuspended in 100 μl of buffer (50 mM TRIS-K$^+$, pH 8.2, 5 mM McCl$_2$, 1 mM EDTA) with proteinase inhibitors (1 mM PMSF, 10 μg/ml leupeptin) and frozen at −80° C. The activity of Rubisco LSMT was determined as described previously (Wang et al., "Affinty purification of ribulose-1,5-bisphosphate carboxylase/oxygenase large subunit N-methyltransferase," *Prot. Expr. Pur.* 6:528–536 (1995)).

For Western analysis protein extracts prepared as described above were separated by SDS-PAGE (15% acrylamide) and trnsferred to PVDF-membranes (Millipore Corp). The membranes were probed with antibody raised against the precursor form of pea Rubisco LSMT expressed in *E. coli.*

Example 7
Isolation of rbcMT-S cDNA.

The high homology between pea and tobacco Rubisco LSMT enabled the inventor to design Rubisco LSMT-specific primers for amplifying a 786-bp fragment (S25', FIG. 1D) from a spinach first-strand cDNA pool reverse-transcribed from total RNA isolated from spinach leaves. Cloning and sequencing of the 786-bp fragment showed that it was a truncated rbcMT-S cDNA which lacked 5' and 3'ends. The remaining 5' and 3' sequences were obtained by 5' and 3' RACE, respectively (for review see Forhman, "RACE: rapid amplification of cDNA ends," *In PCR protocols: a guide to methods and applications*, pp.28–38, Innis et al., eds. Academic Press, San Diego (1990)).

For 5'RACE using an rbcMT-S-specific primer (SR-3, FIG. 2) for first-strand cDNA synthesis and a second nested gene-specific antisense primer (SR-5, FIG. 2) for PCR amplification, resulted in the identification of two 5'RACE products (836-bp and 848-bp fragments) after sequencing, one with a 12-bp insertion designated as S40', and the other without the insertion designated as S38'. In the region where the 5'RACE products and the PCR product (S25') have sequence in common, complete sequence identity was observed and 118-bp overlapped in the cDNA sequences excepting the 12-bp insertion in S40' (FIG. 2).

For 3'RACE using an adapter-primer (AP-1) for first-strand cDNA synthesis and also as a reverse primer, and SF-9 as the rbcMT-S-specific primer for PCR amplification, a single 761-bp PCR product was obtained. Sequence analysis confinmed the identity of the 3'RACE product as encoding the predicted 3' portion of the rbcMT-S protein including the 3' untranslated region (FIG. 1D, FIG. 2). Given these overlapping clones, the inventor was able to assemble the two cDNA sequences (S40 and S38) of the rbcMT-S as shown in the FIG. 1B and FIG. 2.

Both rbcMT-S cDNAs contain a 5' leader of 31-nt and encode for proteins of 495-aa (S40) and 491-aa (S38) with predicted molecular mass of 55.5 kD for S40 and 55.0 kD for S38, which are similar to that of pea (55.0 kD) and tobacco (56.0 kD) (FIG. 3). The deduced rbcMT-S proteins contain four potential N-linked glycosylation site which fit the consensus sequence Asn-Xaa-Ser/Thr (NXS/T), one of which is conserved in the pea and tobacco Rubisco LSMTs (FIG. 3), and like that of pea and tobacco, they also contain five imperfect copies of a motif similar to leucine-rich repeats (LRR) (FIG. 3) (Kobe et al., "The leucine-rich repeat: a versatile binding motif," *Trends Biochem. Sci.,* 19:415–21 (1994)).

Example 8
Characterization of rbcMT-S.

The rbcMT-S covering the entire coding region was cloned and sequenced in the overall length of 3144-bp (FIG.

2). Comparison of the genomic DNA and cDNA sequences allowed the precise location of the six exons and five introns to be mapped (FIG. 1A). It has the similar genomic organization of the tobacco Rubisco LSMT gene (rbcMT-T). The size of the exons is fairly constant while that of the introns is quite variable. Intron III of rbcMT-S occurs at a position corresponding to the 12-bp insertion in the rbcMT-S S40 cDNA (FIG. 2). An identical 12-bp sequence was found to be present at the 3' end of the intron. Examination of the DNA sequence of this intron and flanking regions suggested that either of two 3'splice sites (separated by the 12-bp sequence) is utilized during splicing of the rbcMT-S transcripts. Thus, as illustrated in FIG. 4, when the intron III sequence is completely removed, S38 mRNA encoding a 55.0 kD polypeptide is produced. However, if splicing occurs at the alternative site, S40 mRNA that retains a 12-nt portion of the 3' end of the intron III is generated, and subsequently a 4-amino acid longer polypeptide of 55.5 kD is produced.

A sequence comparison between the rbcMT-S gene and a *Drosophila tra* gene (O'Neil et al., "Interspecific comparison of the transformer gene of Drosophila reveals an unusually high degree of evolutionary divergence," *Genetics* 131:113–128 (1992)) which has been studied for alternative 3' splicing events (Mckeown, "Alternative mRNA splicing," *Annu. Rev. Cell Biol.* 8:133–155 (1992)) shows two striking TC-rich regions of primary sequence homology between these genes [SEQ ID NOS.: 11–14] (CTTTTTCTC and TCTTTTTCCTTGTTCCT for rbcMT-S, and TCTTTTTGTT and TTTTTTTTCTC for tra) in the region preceding the regulated splice site of both genes, and what is likely to be the regulated splice site of rbcMT-S.

Figure 5:
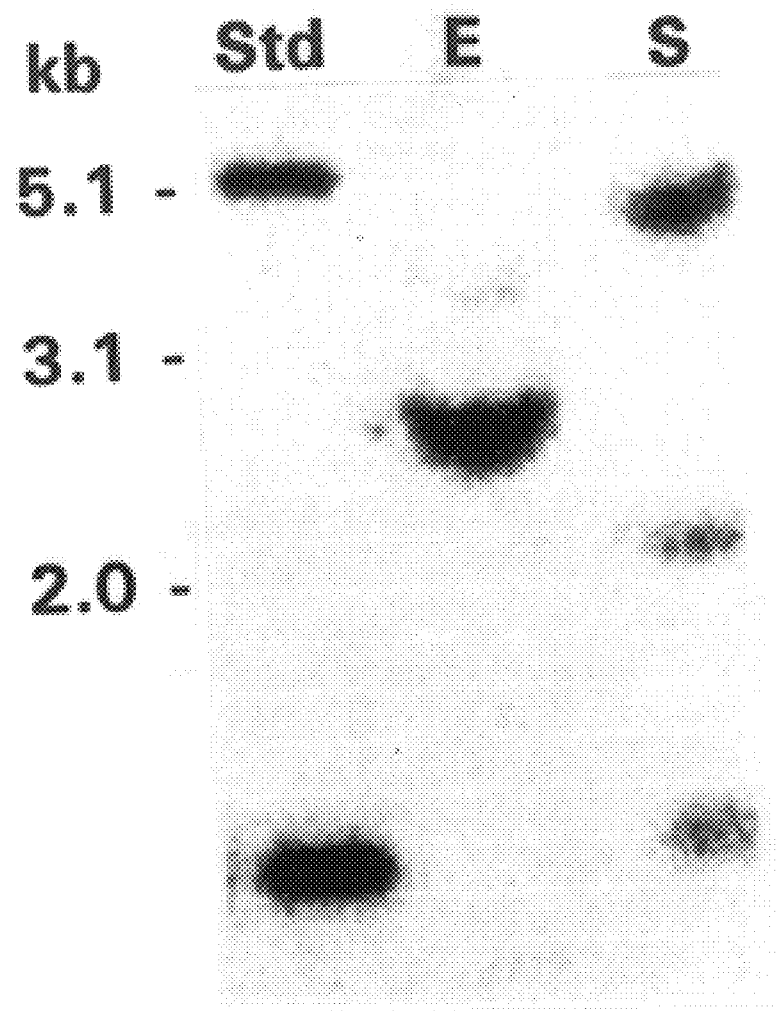
FIG. 5 is an analysis of the spinach genomic DNA. An aliquot of 20 μg of spinach genomic DNA was digested with ScaI and EcoRI respectively, electrophoresed on a 0.7% agarose gel and processed for DNA gel-blot analysis by hybridization to the rbcMT-S cDNA probe labeled with digoxigenin-UTP. A rbcMT-S cDNA clone in BlueScript II KS(+) digested with EcoRI corresponding to one copy was used for copy number reconstitution.

Southern blot analysis suggests that the rbcMT-S is a single copy gene. FIG. 5 shows hybridization of probe I of a $^{32}$P-labeled rbcMT-S cDNA fragment (FIG. 1C) to spinach genomic DNA digested with EcoRI and ScaI. Probe I detected a predicted major 2424-bp EcoRI fragment. Additionally, a predicted 876-bp and two other ScaI fragments were also detected (FIG. 5). The intensity of the signals in each lane is equivalent to a single copy standard (Croy et al., "Plant Nucleic Acids," In: Croy, R. R. D. (eds.) Plant Molecular Biology, pp. 21–48. BIOS Scientific Publishers Limited, Oxford (199x)) on the left side of the blot. Therefore, we conclude that rbcMT-S is a single copy gene in the spinach genome as rbcMT-T is in the tobacco genome.

Example 9

The rbcMT-S mRNA present in vivo and *E. coli* expression in vitro.

Figure 6:
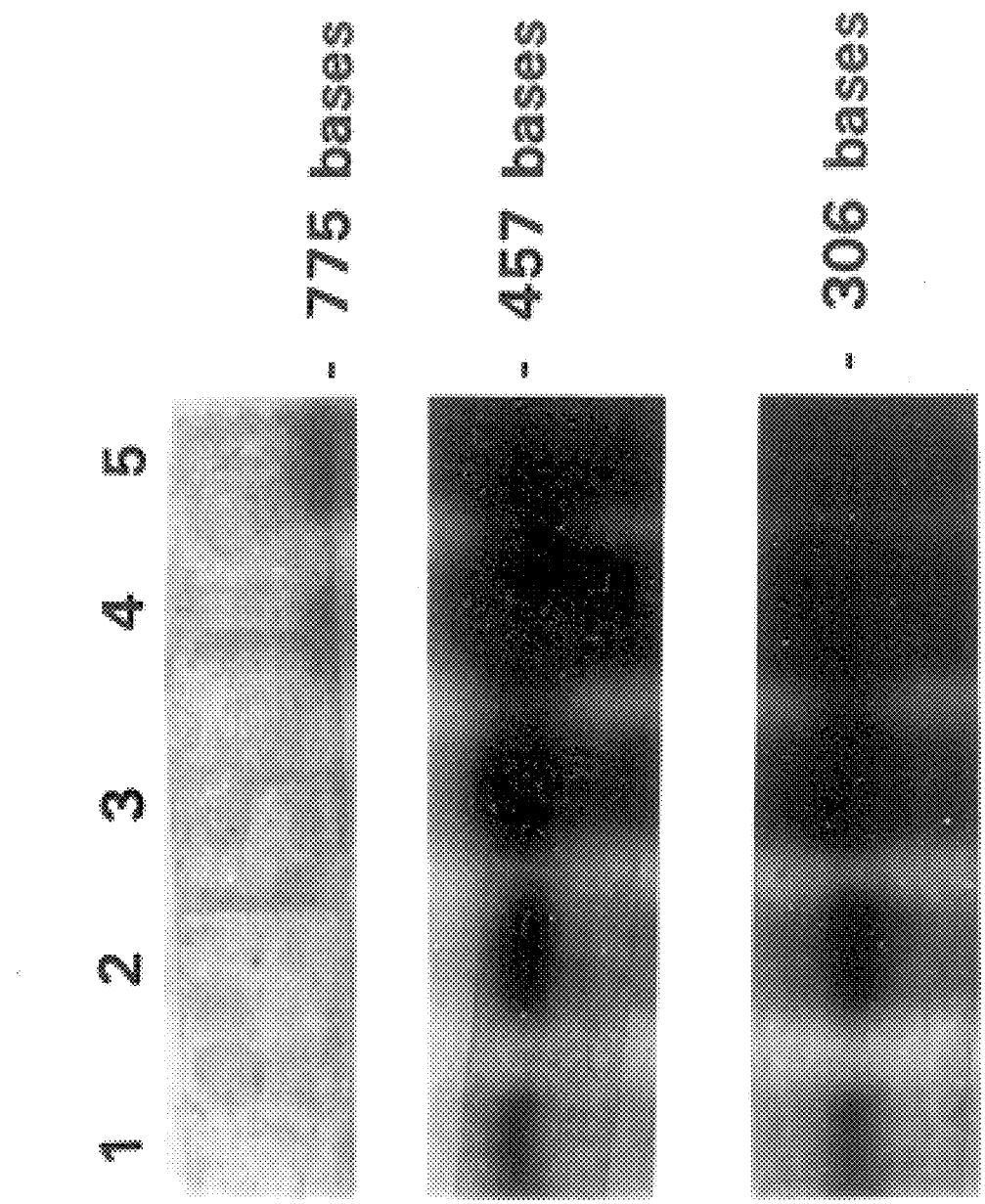
FIG. 6 shows expression of both S38 and S40 mRNA in spinach leaves. RNase protection assays using a 785-nt antisense riboprobe designed to protect a 775-nt of the S40 mRNA from nt-455 to nt-1229, and a 306-nt and 457-nt of the S38 mRNA from nt-455 to nt-760 and from nt-761 to nt-1217 respectively, were carried out. Lanes 1, 2, 3, 4 and 5 are 2.5, 5, 10, 20 and 20 μg of spinach leave total RNA. After hybridization all but lane 5 were digested with 1:100 dilution of RNases. Lane 5 was digested with a 1:50 dilution of RNases (Ambion).

To determine whether both S38 and S40 mRNA are present in the spinach leaves, total RNA from spinach leaves was subjected to an RNase protection analysis using probe II directed toward the middle region of both S38 and S40 mnRNAs (FIG. 1C), where the auxon is present in S40 mRNA. Probe II was designed to protect a single fragment (775-nt) of S40 mRNA and two fragments (306-nt and 457-nt) of S38 mRNA. FIG. 6 shows that S38 mRNA is 20 fold more than S40 mRNA in spinach leaves based on quantitative analysis with a PhosphorImager 445SI (Molecular Dynamic). S40 mRNA is very low in abundance but detectable when high concentrations of total RNA are used. However, S38 and S40 mRNAs are undetectable in spinach roots, stems, and flowers by RNase protection assay (data not shown).

Figure 7:
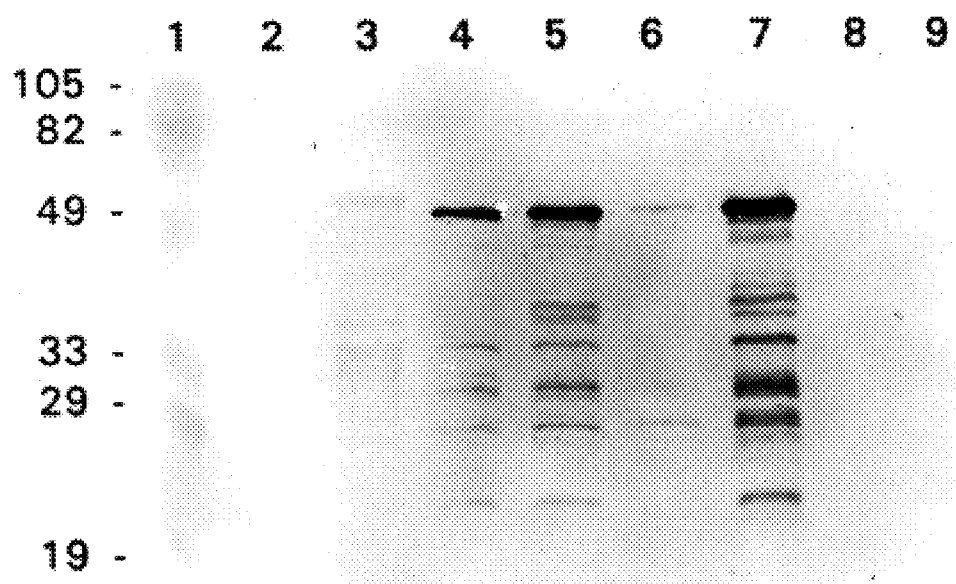
FIG. 7A is a Western blot analysis of S-40, S-38, P-55 and P-55–174 mRNAs expressed in *E. coli*. Lane 1, standard markers; lanes 2 and 3, S-40; lanes 4 and 5, P-55; lanes 6 and 7, P-55-174; lanes 8 and 9, S-38; lanes 2, 4, 6 and 8, soluble protein; lanes 3, 5, 7 and 9, insoluble protein.
FIG. 7B is a bar graph representing Rubisco LSMT activity from the different constructs corresponding to the lanes in FIG. 7A.
Figure 7B:
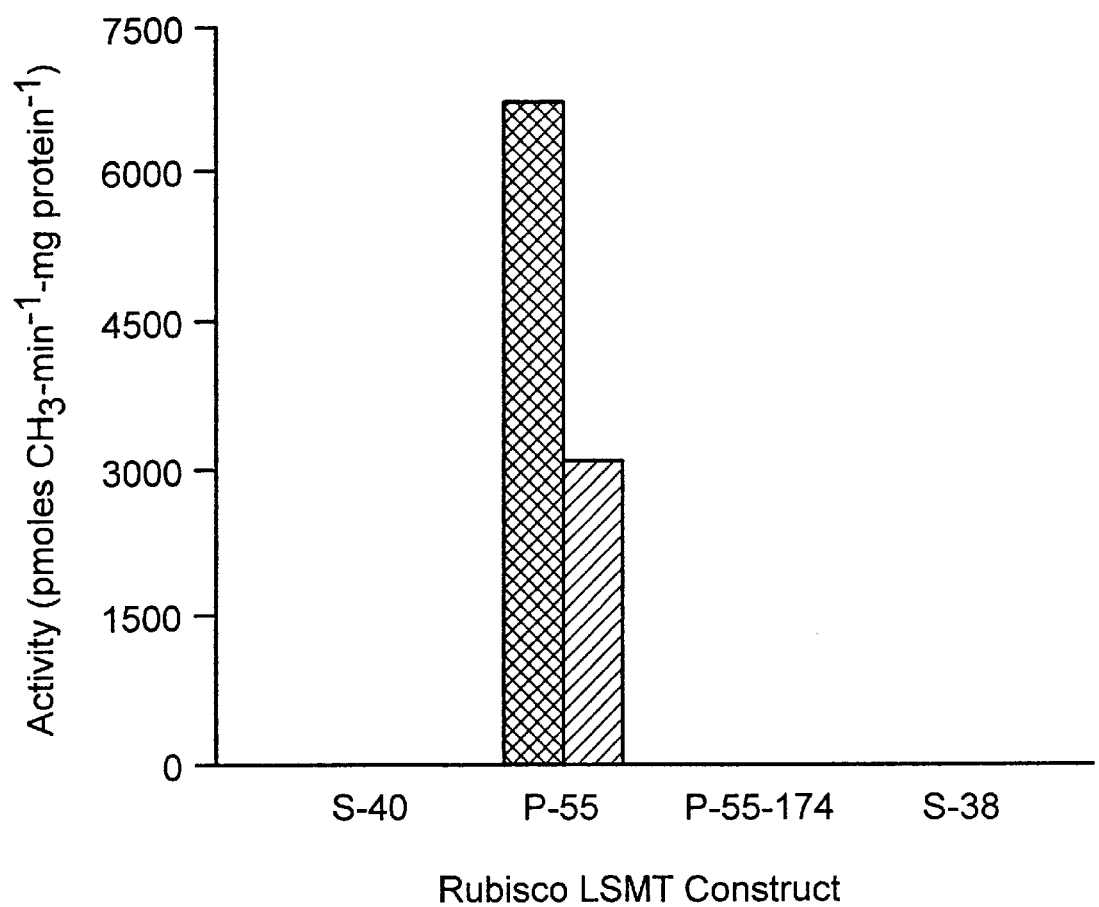

In vitro bacterial expression of the S40 cDNA (S-40) using a pET expression vector did yield a protein (FIG. 7A) at detectable levels but with undetectable activity (FIG. 7B). Furthermore, engineering of the 4 amino acid insert encoded by the 12-bp auxon into the corresponding position in pea Rubisco LSMT (P-55), and bacterial expression of the engineered pea Rubisco LSMT (P-55-174, FIG. 7A) demonstrated that the 4 amino acid insert resulted in complete inactivation of pea Rubisco LSMT activity (FIG. 7B). Therefore, alternative 3' mRNA splicing may result in the inactivation of S40 LSMT. Investigation of the mechanism for inactivation of S38 LSMT is still under way. For some unknown reason, bacterial expression of S38 cDNA (S-38) has been unsuccessful (FIG. 7A).

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art. Furthermore, all of the publications, patents and patent applications cited herein are incorporated by reference in their entirety.

What is claimed is:

1. An isolated Ribulose-1,5-bisphosphate carboxylase/oxygenase large subunit methyltransferase (Rubisco LSMT) enzyme which is encoded by an isolated Rubisco LSMT gene, wherein said gene is derived from a plant with a des(mehyl) lysyl residue at the Lys-14 position in the large subunit (LS) of Rubisco.

2. The isolated enzyme of claim 1, wherein said isolated Rubisco LSMT gene is a spinach Rubisco LSMT gene.

3. The isolated enzyme of claim 1, wherein said gene encodes amino acid sequence S38 or S40 (SEQ ID NOs: 16 and 17), as set forth in FIG. 2.

4. The isolated enzyme of claim 1, wherein said gene has the nucleotide sequence of SEQ ID NO: 15, as set forth in FIG. 2.

* * * * *